US009107819B2

(12) United States Patent
Haeusler et al.

(10) Patent No.: US 9,107,819 B2
(45) Date of Patent: Aug. 18, 2015

(54) WATER INSOLUBLE POLYMER: INDIGESTIBLE WATER-SOLUBLE POLYSACCHARIDE FILM COATINGS FOR COLON TARGETING

(75) Inventors: Olaf Haeusler, Fletre (FR); Daniel Wils, Morbecque (FR); Juergen Siepmann, Phalempin (FR); Youness Karrout, Lille (FR)

(73) Assignee: ROQUETTE FRERES, Lestrem (FR)

( * ) Notice: Subject to any disclaimer, the term of this patent is extended or adjusted under 35 U.S.C. 154(b) by 258 days.

(21) Appl. No.: 13/126,236

(22) PCT Filed: Oct. 27, 2009

(86) PCT No.: PCT/EP2009/064165
§ 371 (c)(1),
(2), (4) Date: Jun. 23, 2011

(87) PCT Pub. No.: WO2010/049432
PCT Pub. Date: May 6, 2010

(65) Prior Publication Data
US 2011/0256230 A1    Oct. 20, 2011

(30) Foreign Application Priority Data

Oct. 27, 2008  (EP) .................................. 08305740

(51) Int. Cl.
| | | |
|---|---|---|
| *A61K 9/28* | (2006.01) | |
| *A61K 47/36* | (2006.01) | |
| *A61K 47/38* | (2006.01) | |
| *A61P 1/00* | (2006.01) | |
| *A61K 9/00* | (2006.01) | |

(52) U.S. Cl.
CPC .............. *A61K 9/0053* (2013.01); *A61K 9/2826* (2013.01); *A61K 9/2846* (2013.01); *A61K 47/36* (2013.01)

(58) Field of Classification Search
CPC . A61K 9/0053; A61K 9/2826; A61K 9/2846; A61K 47/36
See application file for complete search history.

(56) References Cited

U.S. PATENT DOCUMENTS

| | | | |
|---|---|---|---|
| 6,534,549 | B1 | 3/2003 | Newton et al. |
| 6,630,586 | B1 | 10/2003 | Fouache et al. |
| 7,932,238 | B2 | 4/2011 | Wils et al. |
| 2004/0091537 | A1* | 5/2004 | Miller ........................... 424/471 |
| 2005/0171119 | A1* | 8/2005 | Berwaer et al. ........... 514/255.04 |
| 2005/0220861 | A1 | 10/2005 | Palmer et al. |
| 2008/0057086 | A1* | 3/2008 | Etter .............................. 424/400 |
| 2008/0182821 | A1* | 7/2008 | Wils et al. ........................ 514/58 |
| 2011/0200680 | A1* | 8/2011 | Haeusler et al. ............... 424/489 |
| 2013/0078289 | A1* | 3/2013 | Siepmann et al. ............. 424/400 |

FOREIGN PATENT DOCUMENTS

| | | |
|---|---|---|
| EP | 1006123 | 6/2000 |
| JP | 2006219502 A | 8/2006 |
| JP | 2008536997 A | 9/2008 |
| WO | 99/18938 A | 4/1994 |
| WO | 97/25979 A | 7/1997 |
| WO | 00/28974 A | 5/2000 |
| WO | 00/74655 A | 12/2000 |
| WO | 2007122374 A2 | 11/2007 |
| WO | 2008012573 A1 | 1/2008 |

OTHER PUBLICATIONS

Meissner et al: "Alternative drug delivery approaches for the therapy of inflammatory bowel disease", J. Phann. Sci. 97 (2008) 2878-2891.
Bondesen: "Intestinal fate of 5-aminosalicylic acid: regional and systemic kinetic studies in relation to inflammatory bowel disease", Phannacol. Toxicol. 81 (Suppl2) (1997) 1-28.
Lamptrecht A et al: "Carrier systems for the treatment of inflammatory bowel disease", Drugs Fut. 27 (2002) 961-971.
Haupt S et al: "The colon as a possible target for orally administered peptide and protein drugs", Crit. Rev. Ther. Drug Carrier Syst. 19 (2002) 499-551.
Cummings et al: "In vivo studies of amylose- and ethycellulose-coated (I3C) glucose microspheres as a model for drug delivery to the colon", J. Control. Release 40 (1996) 123-131.
Milojevic S et al: "Amylose as a coating for drug delivery to the colon: Preparation and in vitro evaluation using 5-aminosalicylic acid pellets", J. Control. Release 38 (1996) 75-84.
Milojevic S et al: "Amylose as a coating for drug delivery to the colon: Preparation and in vitro evaluation using glucose pellets", J. Control. Release 38 (1996) 85-94.
Yang et al: "Fix, Colon-specific drug delivery: new approaches and in vitro/in vivo evaluation", Int. J. Phann. 235 (2002) 1-15.
Leong CW et al: "The formation of colonic digestible films of amylase and ethylcellulose from aqueous dispersions at temperatures below 37° C.", Eur. J. Phann. Biophann. 54 (2002) 291-297.
Siew et al: "Amylose formulations for drug delivery to the colon: a comparison of two fermentation models to assess colonic targeting performance in vitro", Int. J. Phann. 273 (2004) 129-134.
Siew et al: "The Properties of amylose-ethylcellulose films cast from organic-based solvents as potential coatings for colonic drug delivery", Eur. J. Phann. Sci. 11 (2000) 133-139.
Gazzaniga A et al: "Oral delayed-release system for colonic specific delivery", Int. J. Phann. 108 (1994) 77-83.
Gazzaniga A et al: Oral Chronotopic drug delivery systems: Achievement of time and/or site specificity, Eur. J. Phann Biophann. 40 (1994) 246-250.
Sangalli A et al: In vitro and in vivo evaluation of an oral system for time and/or site-specific drug delivery, J. Control. Release 73 (2001) 103-110.
Gazzaniga A et al: "Time-controlled oral delivery systems for colon targeting", Expert Opinion on Drug Delivery 3 (5) (2006) 583-597.

(Continued)

*Primary Examiner* — Abigail Fisher
(74) *Attorney, Agent, or Firm* — Young & Thompson

(57) ABSTRACT

A controlled release pharmaceutical dosage form for controlled release of an active ingredient, includes an active ingredient coated by a polymeric mixture of: at least a water insoluble polymer; and at least an indigestible water-soluble oligosaccharide. The use and method of making the same are also described.

14 Claims, 23 Drawing Sheets

(56) References Cited

OTHER PUBLICATIONS

Lecomte F et al: "Polymers blends used for the aqueous coating of solid dosage forms: importance of the type of plasticizer", J. Control. Release 99, (2004) 1-13.
Lecomte F et al: "Polymer blends used for the coating of multiparticulates: Comparison of aqueous and organic coating techniques", Pharm. Res. 21 (5), (2004) 882-890.
Sinha VR et al: Microbially triggered drug delivery to the colon, Eur. J. Pharm. Sci. 18 (2003) 3-18.
Sinha VR et al: Polysaccharides in colon-specific drug delivery, Int. J. Pharm. 224 (2001) 19-38.
Friend DR: "New oral delivery systems for treatment of inflammatory bowel disease", Adv. Drug Deliv. Rev. 57 (2005) 247-265.
Yamani et al: "Decreased faecal exoglycosidase activities identify a subset of patients with active Crohn's Disease", Clin. Sci. 83 (1992) 409-415.
Carette O et al: "Bacterial enzymes used for colon-specific drug delivery are decreased in active Crohn's Diseases", Digestive Diseases and Sciences 40 (1995) 2641-2646.
Favier C et al:"Fecal P—Dgalactosidase production and bifidobacteria are decreased in Crohn's Disease", Digestive Diseases and Sciences 42 (1997) 817-822.
Siccardi D et al: "Regulation od intestinal epithelial function: a link between opportunities for macromolecular drug and inflammatory bowel disease, Ad"v. Drug Deliv. 57 (2005) 219-235.
Siew LF et al: "The potential of organic-based amylose ethylcellulose film coatings as oral colon-specific drug delivery systems", AAPS PharmSciTech 1 (3) (2000) article 22.
Wattas PJ et al: ":Colonic drug delivery", Drug Dev. Ind. Pharm 23 (9) (1997) 893-913.
Davis SS et al: "Transit of pharmaceutical dosage forms through the small intestine", Gut 27 (1986) 886-892.
Wilding I.R. et al: "Gastrointestinal spread of oral prolonged-release mesalazine microgranules (Pentasa) dosed as either tablets or sachet", Aliment. Pharmacol. Ther. 14 (200) 163-169.
Hoover R et al: Composition, structure, functionality, and chemical modification of legume starches: a review, Can. J. Physiol. Pharmacol. vol. 69, 1991 79-92.
Hedley CL et al: "Developing novel pea starches", Proceedings of the symposium of the industrial biochemistry and biotechnology group of the biochemical society (1996) 77-87.
European Search Report, dated Aug. 11, 2009, in EP 08 30 5740.
International Report, dated Jan. 19, 2010, in PCT/EP2009/064165.
Meissner et al: "Alternative drug delivery approaches for the therapy of inflammatory bowel disease", J. Pharm. Sci. 97 (2008) 2878-2891.
Bondesen: "Intestinal fate of 5-aminosalicylic acid: regional and systemic kinetic studies in relation to inflammatory bowel disease", Pharmacol. Toxicol. 81 (Suppl2) (1997) 1-28.
Cummings et al: "In vivo studies of amylose- and ethycellulose-coated (13C) glucose microspheres as a model for drug delivery to the colon", J. Control. Release 40 (1996) 123-131.
Yang et al: "Fix, Colon-specific drug delivery: new approaches and in vitro/in vivo evaluation", Int. J. Pharm. 235 (2002) 1-15.
Leong CW et al: "The formation of colonic digestible films of amylase and ethylcellulose from aqueous dispersions at temperatures below 37° C", Eur. J. Pharm. Biopharm. 54 (2002) 291-29.
Siew et al: "Amylose formulations for drug delivery to the colon: a comparison of two fermentation models to assess colonic targeting performance in vitro", Int. J. Pharm. 273 (2004) 129-134.
Siew et al: "The Properties of amylose-ethylcellulose films cast from organic-based solvents as potential coatings for colonic drug delivery", Eur. J. Pharm. Sci. 11 (2000) 133-139.
Gazzaniga A et al: "Oral delayed-release system for colonic specific delivery", Int. J. Pharm. 108 (1994) 77-83.
Gazzaniga A et al: Oral Chronotopic drug delivery systems: Achievement of time and/or site specificity, Eur. J. Pharm Biopharm. 40 (1994) 246-250.
Favier C et al:"Fecal B-D-galactosidase production and bifidobacteria are decreased in Crohn's Disease", Digestive Diseases and Sciences 42 (1997) 817-822.
Siccardi D et al: Regulation of intestinal epithelial function: a link between opportunities for macromolecular drug delivery and inflammatory bowel disease, Adv. Drug Deliv. Rev. 57 (2005) 219-235.
International Report, dated Jan. 19, 2010, in PCT/EP2009/064166.
Akhgari et al., "Permeability and swelling studies on free films containing inulin in combination with different polymethacrylates aimed for colonic drug delivery", European Journal of Pharmaceutical Sciences, 2006, vol. 28, pp. 307-314.
Ravi et al., "Novel colon targeted drug delivery system using natural polymers", Indian Journal of Pharmaceutical Sciences, 2008, vol. 70, Issue 1, pp. 111-113.
Vandamme et al., "The use of polysaccharides to target drugs to the colon", Corbohydrate Polymers, vol. 48, Issue 3, 2002, pp. 219-231.
Translation of Japanese Office Action, dated Dec. 3, 2013, from corresponding JP application.

* cited by examiner

6a)
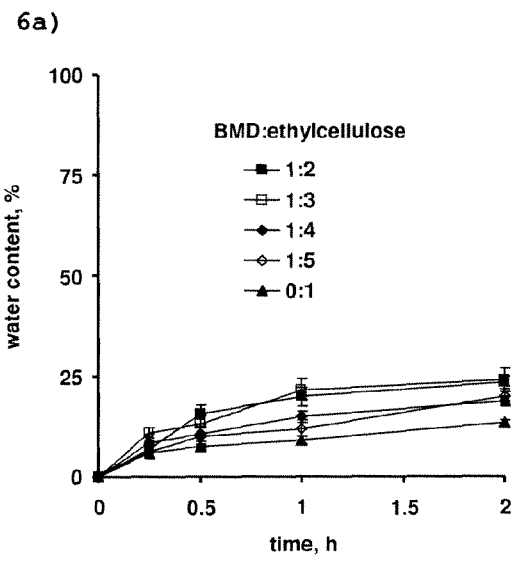
6b)
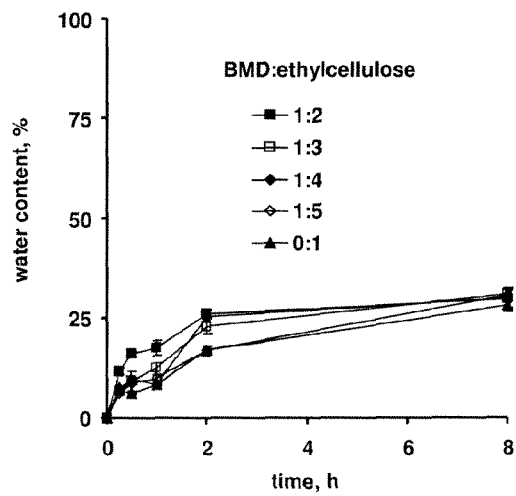
Figure 6
7a)
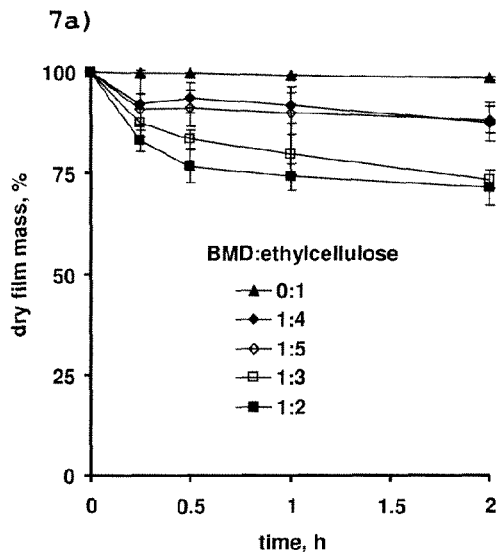
7b)
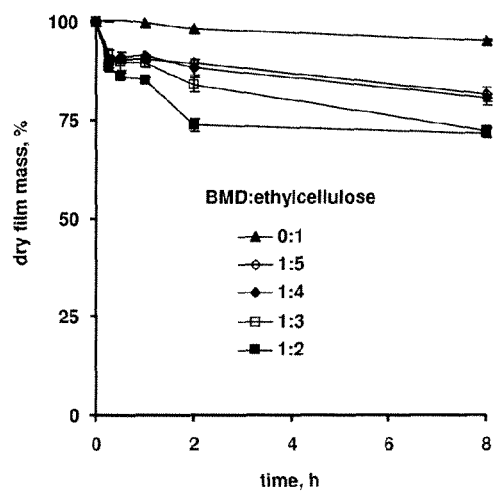
Figure 7

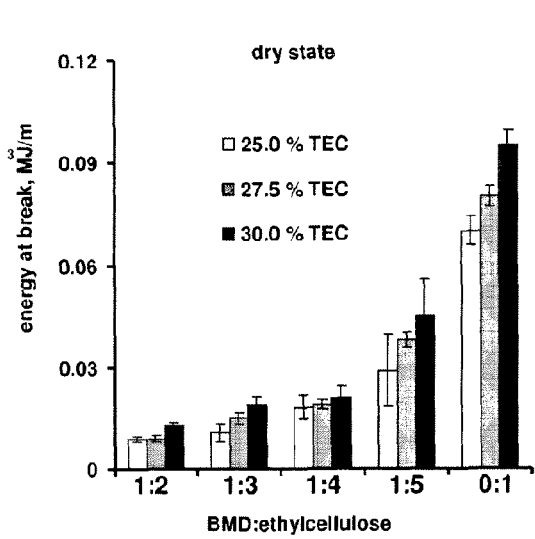
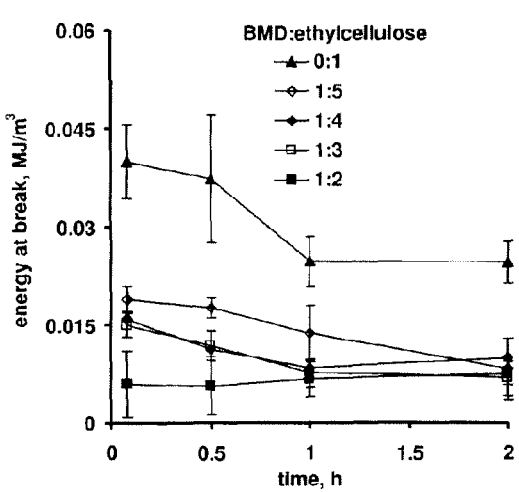
Figure 8
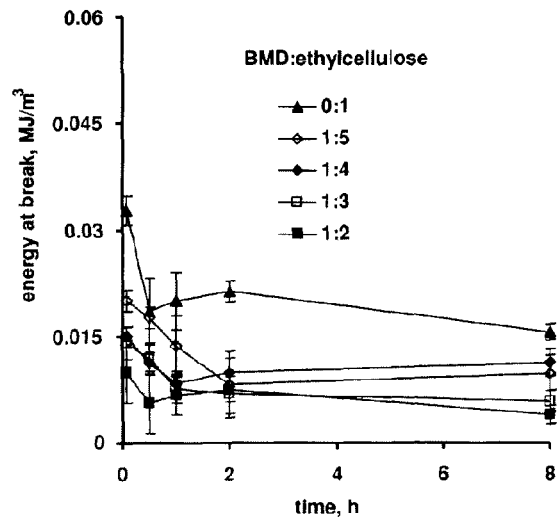
Figure 9

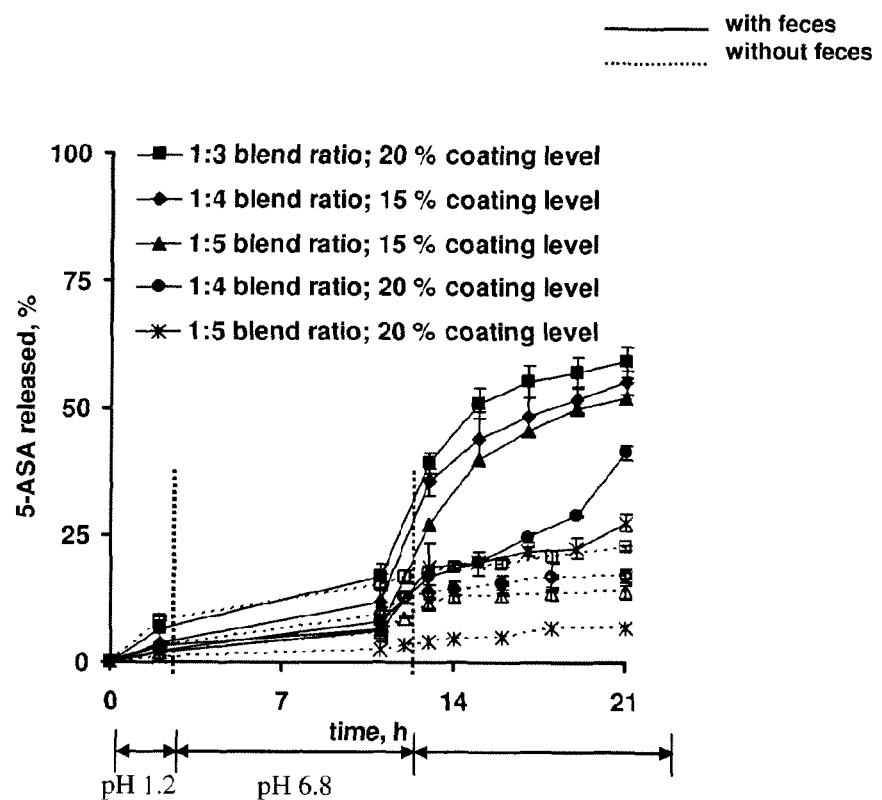
——— with feces
·········· without feces
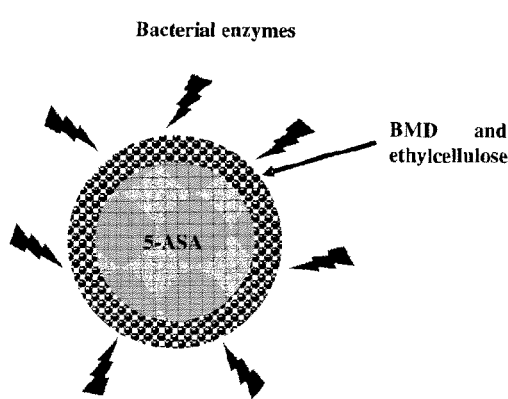
Figure 17

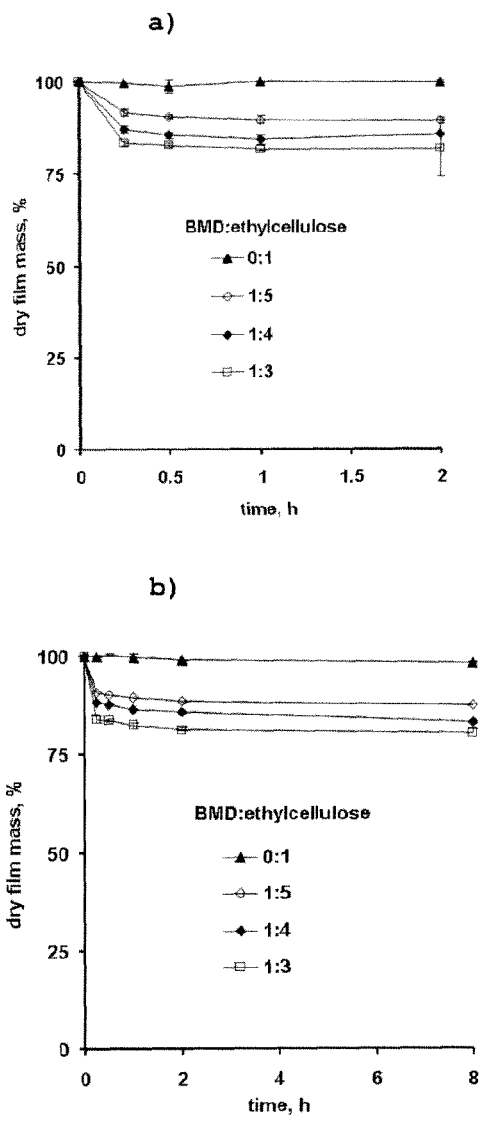
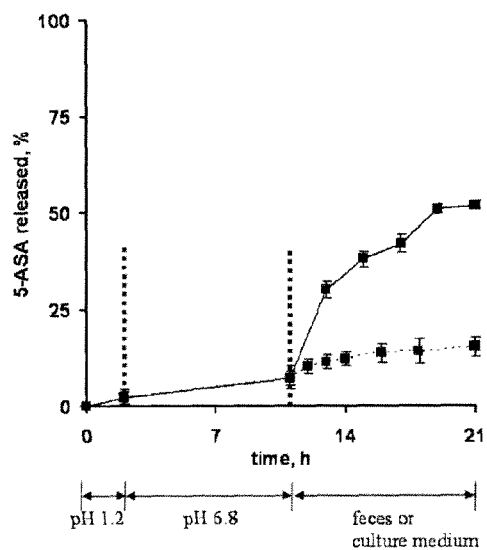
Figure 21
Figure 22

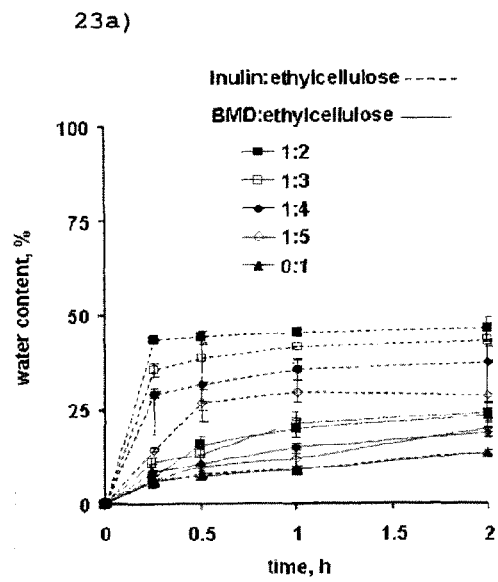
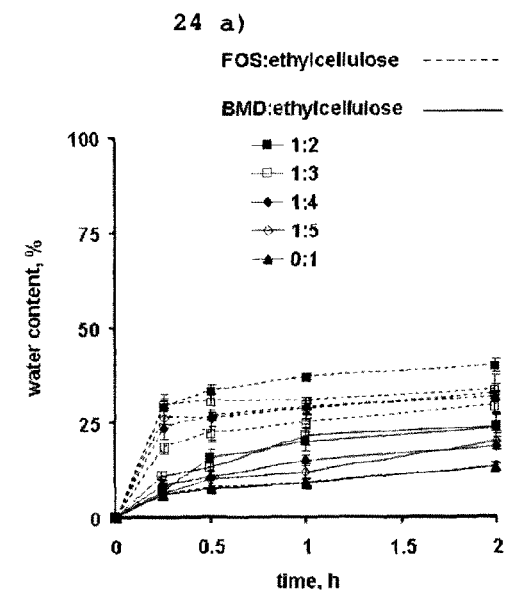
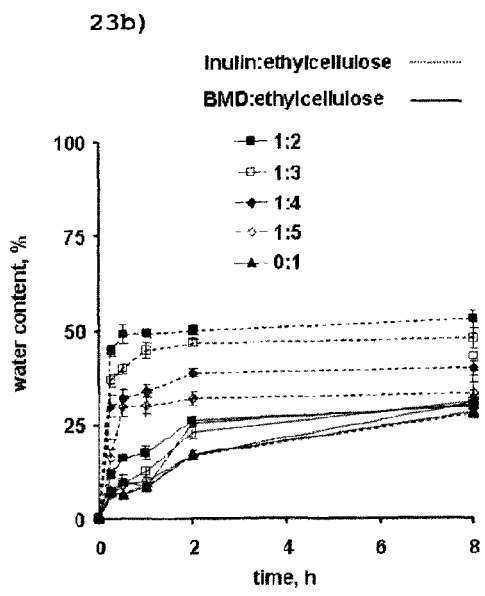
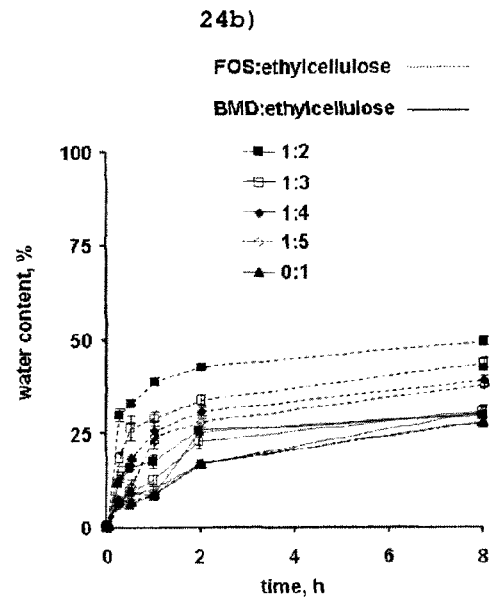
Figure 23                                   Figure 24

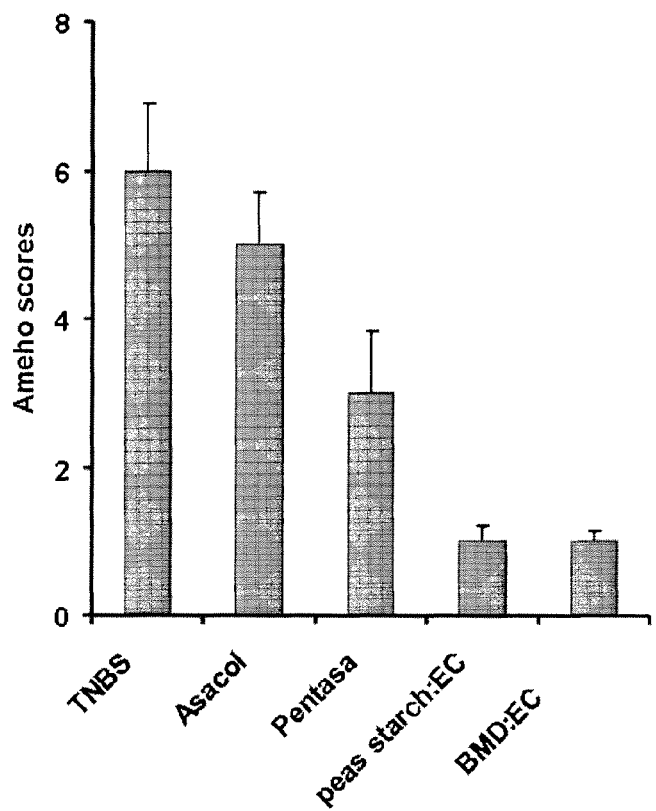

Figure 28

Ameho score
Denotes a p=1 between Asacol® and TNBS-induced colitis.
Denotes a p=0.57 between Pentasa® and TNBS-induced colitis.
Denotes a p=0.0038 between BMD:EC coated pellets and TNBS-induced colitis.
Denotes a p=0.024 between peas starch:EC coated pellets and TNBS-induced colitis
Denotes a p=0.006 between BMD:EC coated pellets and Pentasa®.
Denotes a p=0.016 between peas starch:EC coated pellets and Pentasa®.

Control
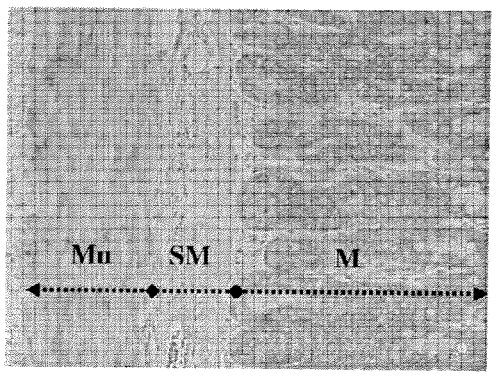
TNBS
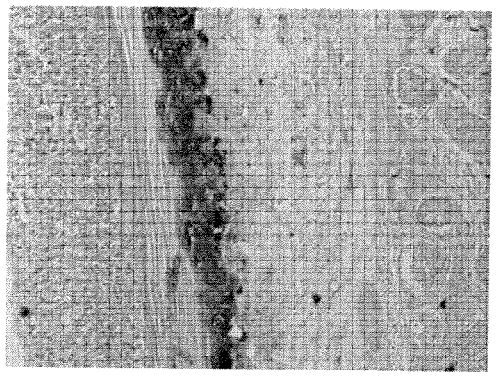
NUTRIOSE:EC coated pellets
pellets
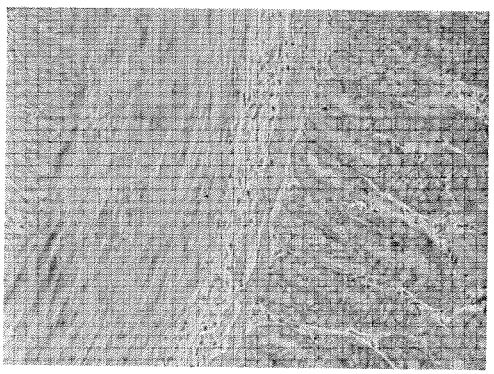
peas starch:EC coated
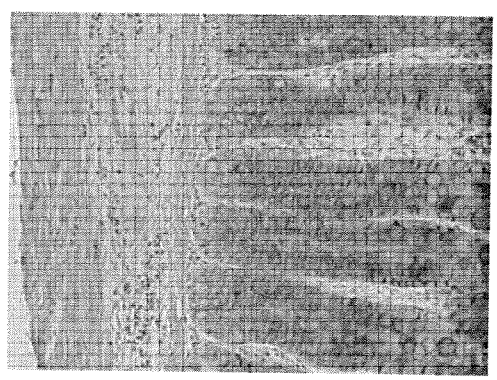
Pentasa®
Asacol®
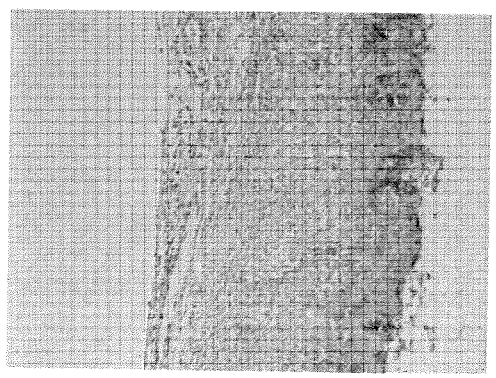
Figure 29

WATER INSOLUBLE POLYMER: INDIGESTIBLE WATER-SOLUBLE POLYSACCHARIDE FILM COATINGS FOR COLON TARGETING

FIELD OF THE INVENTION

The present invention relates to a controlled release delivery dosage form for the controlled delivery of active ingredient(s). The present invention also relates to the use and method for making the same.

BACKGROUND OF THE INVENTION

Colon targeting can be very helpful for many pharmacotherapies, including the treatment of inflammatory bowel diseases, such as Crohn's Disease (CD) and Ulcerative Colitis (UC).

If a locally acting drug is orally administered using a conventional pharmaceutical dosage form, the latter rapidly dissolves in the contents of the stomach, the drug is released and likely to be absorbed into the blood stream. This leads to elevated systemic drug concentrations and, thus, an increased risk of undesired side effects and at the same time to low drug concentrations at the site of action in the colon, resulting in poor therapeutic efficiency. These restrictions can be overcome if drug release is suppressed in the stomach and small intestine and time-controlled in the colon. This type of site-specific drug delivery to the colon might also offer an interesting opportunity for protein and peptide drugs to get absorbed into the systemic circulation upon oral administration.

To allow for colon targeting, the drug can for instance be embedded within a polymeric matrix former, or drug-loaded tablets or pellets such as spherical beads, approximately 0.5-1 mm in diameter; can be coated with a polymeric film. In the upper gastro intestinal tract (GIT), the permeability of the polymeric networks for the drug should be low, whereas the macromolecular barriers must become permeable once the colon is reached. This increase in drug permeability of the polymeric networks at the site of action might be induced by: (i) a change in the pH of the contents of the GIT, (ii) a change in the quality and/or quantity of enzymes along the GIT, or (iii) significant structural changes within the dosage form occurring after a pre-determined lag-time (e.g. crack formation in poorly permeable film coatings providing pulsatile drug release patterns). Alternatively, drug release might already start in the stomach and continue throughout the GIT, at a rate that is sufficiently low to assure that drug is still inside the dosage form once the colon is reached.

An attempt to solve the problem of colon targeting is disclosed in US2005220861A that relates to a controlled release formulation for delivery of prednisolone sodium metasulphobenzoate. The formulation comprises prednisolone sodium metasulphobenzoate surrounded by a coating comprising glassy amylose, ethyl cellulose and dibutyl sebacate, wherein the ratio of amylose to ethyl cellulose is from (1:3.5) to (1:4.5) and wherein the amylose is corn or maize amylose. In contrast to the American patent application number US2005220861, the system described in the present invention is adapted to the disease state of patients. This is a very crucial aspect, because to allow for colon targeting the dosage form must become more permeable for the drug once the colon is reached. This can for instance be assured by a preferential degradation of a compound that hinders rapid drug release in the upper gastro intestinal tract. This site-specific degradation can be based on significant differences in the quality and quantity of enzymes present in the upper gastro intestinal tract versus the colon. The compound should not be degraded in the upper gastro intestinal tract (and hinder drug release), but should be degraded in the colon (and, thus, allow for drug release). The performance of this type of advanced drug delivery systems is fundamentally depending on the environmental conditions in the colon of the patients, in particular on the types and concentrations of the enzymes present in the colon. It is well known and has been well documented in the literature that the disease state can significantly affect the quality and quantity of the enzyme secreting microflora in the gastro intestinal tract. This is particularly true for the microflora in the colon of patients suffering from inflammatory bowel diseases: the quality and quantity of the enzymes present in the colon of a patient can, thus, significantly vary from those in a healthy subject. Consequently, the performance of this type of drug delivery systems can significantly be affected by the disease state. Systems that are based on the preferential degradation by enzymes which are not present in sufficient concentrations in the disease state in the colon of the patient fail. The present invention reports for the first time on dosage forms allowing for controlled delivery of active ingredient under pathophysiological conditions: in feces of patients suffering from inflammatory bowel diseases. Thus, the performance of these dosage forms is assured under the given pathophysiological conditions in vivo. This is decisive for the success and safety of the treatment.

U.S. Pat. No. 6,534,549 relates to a method for producing a controlled release dosage form comprising a mixture of a substantially water-insoluble film-forming polymer and amylose in a solvent system comprising (1) water and (2) a water-miscible organic solvent which on its own is capable of dissolving the film-forming polymer is contacted with an active material and the resulting composition dried. The dosage form is particularly suitable for delivering therapeutic agents to the colon. In contrast to the present invention that disclosure addresses drug delivery systems prepared using an organic solvent. This is not the case in the present invention. The use of organic solvents implies several concerns, including toxicity and environmental concerns as well as explosion hazards. Furthermore, the use of amylose implies the extraction of this polymer and its stabilization. Amylose is extracted from starch after an hydrolysis and a purification step. This process is complex and difficulty usable at an industrial level. This formulation doesn't take into account the drug release kinetics for patients suffering from inflammatory bowel diseases. It has to be pointed out that the types and amounts of bacteria present in the colon of inflammatory bowel disease patients can significantly differ from those in healthy subjects. Thus, the types and amounts of enzymes secreted by these bacteria and being in contact with the drug delivery system can significantly differ. Consequently, the performance of the drug delivery system can significantly differ.

SUMMARY OF THE INVENTION

An object of the present invention is to provide a delivery dosage form to control the rate and extent of delivery of an active ingredient, for example, without limitation an active pharmaceutical ingredient, biological, chemical, nutraceutical, agricultural or nutritional active ingredients.

Another object of the present invention is to provide new polymeric film coatings that allow for site-specific drug targeting to the colon and that may be used for patients suffering from inflammatory bowel diseases as well as for patients with a healthy colon.

A further object of the present invention is to provide new polymeric film coatings having a sufficient mechanical stability to withstand the shear stress they are exposed to in the upper GIT (due to the gastro intestinal motility) and to withstand the potentially significant hydrostatic pressure developed within the dosage forms due to water penetration into the systems upon contact with aqueous media. Indeed, with known polymer coatings, the problem of accidental crack formation can result in premature drug release through water-filled channels.

A further object of the present invention is to provide new polymeric film coatings adjustable to the specific needs of a particular type of drug treatment e.g, osmotic activity of the drug and administered dose.

The present invention provides a controlled release pharmaceutical dosage form for controlled release of an active ingredient, comprising an active ingredient coated by a polymeric mixture of:
at least a water insoluble polymer and
at least an indigestible water-soluble polysaccharide.

Preferably, the polymeric mixture provides a colon targeting release, that is the release of said active ingredient in the colon of patients having a colonic microflora imbalance and in the colon of healthy subjects.

Preferentially the controlled release dosage form is an oral formulation and has a gastric resistance. In a preferred embodiment, the controlled release pharmaceutical dosage form is in a solid, liquid or semi-liquid form. Advantageously the controlled release pharmaceutical dosage form is a solid dispersion. According to the invention, the polymeric mixture is an intimate mix of the water insoluble polymer and the indigestible water-soluble polysaccharide, said indigestible water-soluble polysaccharide doesn't oligosaccharide does not form particulates in the water insoluble polymer.

In an embodiment of the present invention the controlled release delivery dosage form comprising a core, the active ingredient dispersed or dissolved in the core.

In a further embodiment of the present invention, the indigestible water-soluble polysaccharide is selected from the group consisting of xylooligosaccharides, inulin, oligofructoses, fructo-oligosaccharides (FOS), lactulose, galactomannans and suitable hydrolysates thereof, indigestible polydextrose, indigestible dextrins and partial hydrolysates thereof, trans-galacto-oligosaccharides (GOS), xylo-oligosaccharides (XOS), acemannans, lentinans or beta-glucans and partial hydrolysates thereof, polysaccharides-K (PSK), indigestible maltodextrins, and partial hydrolysates thereof, or their mixture.

Preferably, the polymeric mixture contains additionally a polysaccharide such as a legume selected from the group consisting of pea, bean, broad bean and horse bean or cereal starch.

According to another advantageous alternative dosage form, the legume is a plant, for example a variety of pea or of horse bean, giving seeds comprising at least 25%, preferably at least 40%, by weight of starch (dry/dry). Advantageously, the legume is pea.

According to the invention, the indigestible water-soluble polysaccharide is an indigestible maltodextrin or indigestible dextrin having between 15 and 35% of 1→6 glucoside linkages, a reducing sugar content of less than 20%, a polymolecularity index of less than 5 and a number-average molecular mass Mn at most equal to 4500 g/mol.

According to a variant, all or some of the said indigestible maltodextrins are hydrogenated.

According to the invention, the indigestible water-soluble polysaccharide is a branched maltodextrin.

In a further embodiment the indigestible water-soluble polysaccharide:water insoluble polymer ratio in the controlled release delivery dosage form is between 1:2 and 1:8, preferentially 1:3 to 1:6, and more preferentially 1:4 to 1:5.

According to a variant, the core particle has a coating level of 5% to 30%, preferably of 10% to 20%.

In a further embodiment, the polymeric mixture comprises a plasticizer, preferably the plasticizer content is between 25% to 30% w/w referred to the water insoluble polymer content.

Preferably, the water insoluble polymer is selected from the group consisting of ethyl cellulose, cellulose derivatives, acrylic and/or methacrylic ester polymers, polymers or copolymers of acrylate or methacrylate polyvinyl esters, starch derivatives, polyvinyl acetates, polyacrylic acid esters, butadiene styrene copolymers methacrylate ester copolymers, cellulose acetate phtalate, polyvinyl acetate phtalate, shellac, methacrylic acid copolymers, cellulose acetate trimellitate, hydroxypropyl methylcellulose phtalate, zein, starch acetate.

According to a further embodiment the plasticizer is a water soluble plasticizer. Preferably the water soluble plasticizer is selected from the group consisting of polyols (glycerin, propylene glycol, polyethylene glycols), organic esters (phtalate esters, dibutyl sebacate, citrate esters, triacetin), oils/glycerides (castor oil, acetylated monoglycerides, fractionated coconut oil), soya lecithin alone or as a mixture with one another.

In a preferred embodiment, the controlled release dosage form is a multiparticulate dosage form.

The present invention also provides a method for preparing a controlled release pharmaceutical dosage form for controlled release of an active ingredient in the colon of patients having a colonic microflora imbalance or in the colon of healthy subjects, said method comprising:
forming a polymeric mixture of:
at least one water insoluble polymer and
at least an indigestible water-soluble polysaccharides,
coating said active ingredient by the polymeric mixture.

In a further embodiment, the step of coating the active ingredient is a coating step of a core, the active ingredient being dispersed or dissolved in the core and/or the step of coating the active ingredient is a step of dispersing or dissolving the active ingredient in the polymeric mixture.

The present invention also provides a method for preparing a controlled release pharmaceutical dosage form for controlled release of an active ingredient in the colon of patients having a Colonic microflora imbalance or in the colon of healthy subjects, said controlled release dosage form stimulating the growth and/or activity of bacteria in the digestive system, said method comprises:
forming a polymeric mixture of:
at least a water insoluble polymer and
at least an indigestible water-soluble polysaccharide
coating said active ingredient by the polymeric mixture.

Stimulating the growth and/or activity of bacteria in the digestive system is beneficial to the health of the body; this effect is called a Prebiotic effect. Prebiotics are non-digestible ingredients, such as non-digestible carbohydrates, which have a beneficial effect on the health. Non-digestible carbohydrates such as notably xylopolysaccharides, inulin, oligofructoses, fructo-oligosaccharides (FOS), or Branched maltodextrins, are described as having a prebiotic effect.

In a further embodiment, the step of coating the active ingredient is a coating step of a core, the active ingredient being dispersed or dissolved in the core and/or the step of coating the active ingredient is a step of dispersing or dissolving the active ingredient in the polymeric mixture.

The conditions in the gastro intestinal tract of patients suffering from inflammatory bowel diseases (e.g. Crohn's Diseases and Ulcerative Colitis) can significantly differ from those in a healthy subject. The intra- and inter-individual variability can be substantial with respect to the pH of the GIT contents, types and concentrations of enzyme-secreting bacteria as well as to the transit times within the various GIT segments. For instance, considerable amounts of bifidobacteria are generally present in the colon of healthy subjects and are able to degrade complex polysaccharides due to multiple extracellular glycosidases. However, in the disease state their concentration can be significantly reduced. For example, it was shown that the fecal glycosidase activity (especially that of β-D-galactosidase) is decreased in patients suffering from Crohn's Disease and that the metabolic activity of the colonic flora is strongly disturbed in the active disease state. Thus, the impact of the pathophysiology can be crucial and can lead to the failure of the pharmaco-treatment.

To avoid treatment failures for patients suffering from inflammatory bowel diseases, the site-specific drug delivery system must be adapted to the conditions given in the patients' colon. For instance, polymeric film coatings might be used that are degraded by enzymes, which are present in the feces of Crohn's Disease and Ulcerative Colitis patients in sufficient amounts. However, yet it is unclear which type(s) of polymers fulfills these pre-requisites.

Thus, the present invention also provides the use of a colon targeting coating preparation comprising a water insoluble polymer and an indigestible water-soluble polysaccharides, in the manufacture of a medicament for stimulating the growth and/or activity of bacteria in the digestive system. Preferably the invention provides the use of a polymer coating preparation comprising a water insoluble polymer and an indigestible water-soluble polysaccharides, in the manufacture of a medicament for a colon targeting release of an active ingredient in a therapeutic and/or prophylactic treatment of patients suffering from a colonic bacteria imbalance and for stimulating the growth and/or activity of bacteria in the digestive system. In a preferred embodiment, patients suffering from a colonic bacteria imbalance are patients suffering from inflammatory bowel diseases. Indeed, the coating preparation according to the invention provides simultaneously a specific release of an active ingredient in the colon of patients suffering or not of a colonic microflora imbalance and a prebiotic effect, that is, the stimulation of the colonic microflora.

BRIEF DESCRIPTION OF THE DRAWINGS

FIG. 6: Water uptake of thin films consisting of Branched maltodextrin:ethylcellulose blends (the ratio is indicated in the figures) upon exposure to: (a) 0.1 M HCl and (b) phosphate buffer pH 6.8 (TEC content, referred to the ethylcellulose mass: 25% w/w).

FIG. 7: Dry mass loss of thin films consisting of Branched maltodextrin:ethylcellulose (the ratio is indicated in the figures) upon exposure to: (a) 0.1 M HCl and (b) phosphate buffer pH 6.8 (TEC content, referred to the ethylcellulose mass: 25% w/w).

FIG. 8: Effects of the Branched maltodextrin:ethylcellulose blend ratio and initial plasticizer content on the energy required to break thin, polymeric films in the dry state at room temperature.

FIG. 9: Changes in the energy required to break thin branched maltodextrin:ethylcellulose films (the blend ratio is indicated in the figures) upon exposure to: (a) 0.1 M HCl and (b) phosphate buffer pH 6.8 at 37° C. (TEC content, referred to the ethylcellulose mass: 25% w/w).

FIG. 17: 5-ASA release from pellets coated with Branched maltodextrin:ethylcellulose blends (the ratio is indicated in the figure) at 15 or 20% coating level under conditions simulating the transit through the entire GIT, with fecal samples from inflammatory bowel disease patients. The dipping speed was 10 dpm. For reasons of comparison also drug release in culture medium without fecal samples is shown (dotted lines). The cartoon illustrates the principle of the investigated colon targeting approach.

FIG. 21: Dry mass loss kinetics of thin NUTRIOSE:ethylcellulose films upon exposure to: (a) 0.1 M HCl, and (b) phosphate buffer pH 6.8. The polymer:polymer blend ratio (w:w) is indicated in the diagrams. Ethylcellulose was plasticized with 25% dibutyl sebacate.

FIG. 22: 5-ASA release from pellets coated with NUTRIOSE:ethylcellulose 1:4 (ethylcellulose being plasticized with 25% dibutyl sebacate) under conditions simulating the transit through the entire GIT, in the presence (solid curves) and absence (dotted curves) of feces from inflammatory bowel disease patients. The coating level was 15%.

FIG. 23: Water uptake of thin films consisting of Branched maltodextrin:ethylcellulose blends (full lines) and Inulin:ethylcellulose at the following ratios 0:1; 1:2; 1:3; 1/4 and 1:5 and upon exposure to: (a) 0.1 M HCl and (b) phosphate buffer pH 6.8 (TEC content, referred to the ethylcellulose mass: 25% w/w).

FIG. 24: Water uptake of thin films consisting of Branched maltodextrin:ethylcellulose blends (full lines) and FOS:ethylcellulose at the following ratios 0:1; 1:2; 1:3; 1/4 and 1:5 and upon exposure to: (a) 0.1 M HCl and (b) phosphate buffer pH 6.8 (TEC content, referred to the ethylcellulose mass: 25% w/w).

FIG. 28: Ameho scores of rats, receiving: (i) TNBS intrarectally, (ii) TNBS intrarectally and Asacol® pellets orally, (iii) TNBS intrarectally and Pentasa® pellets orally, (iv) TNBS intrarectally and peas starch: ethylcellulose coated pellets orally, (v) TNBS intrarectally and BMD:ethylcellulose coated pellets orally. TNBS was administered intrarectally on day 3. The orally administered dose of 5-ASA was 150 mg/kg/day.

FIG. 29: Representative histological sections (normal transparietal section, ×200) of colon tissues of rats. The different layers are indicated: M—mucosa; SM—submucosa; Mu—muscular layer.

Figure 1:
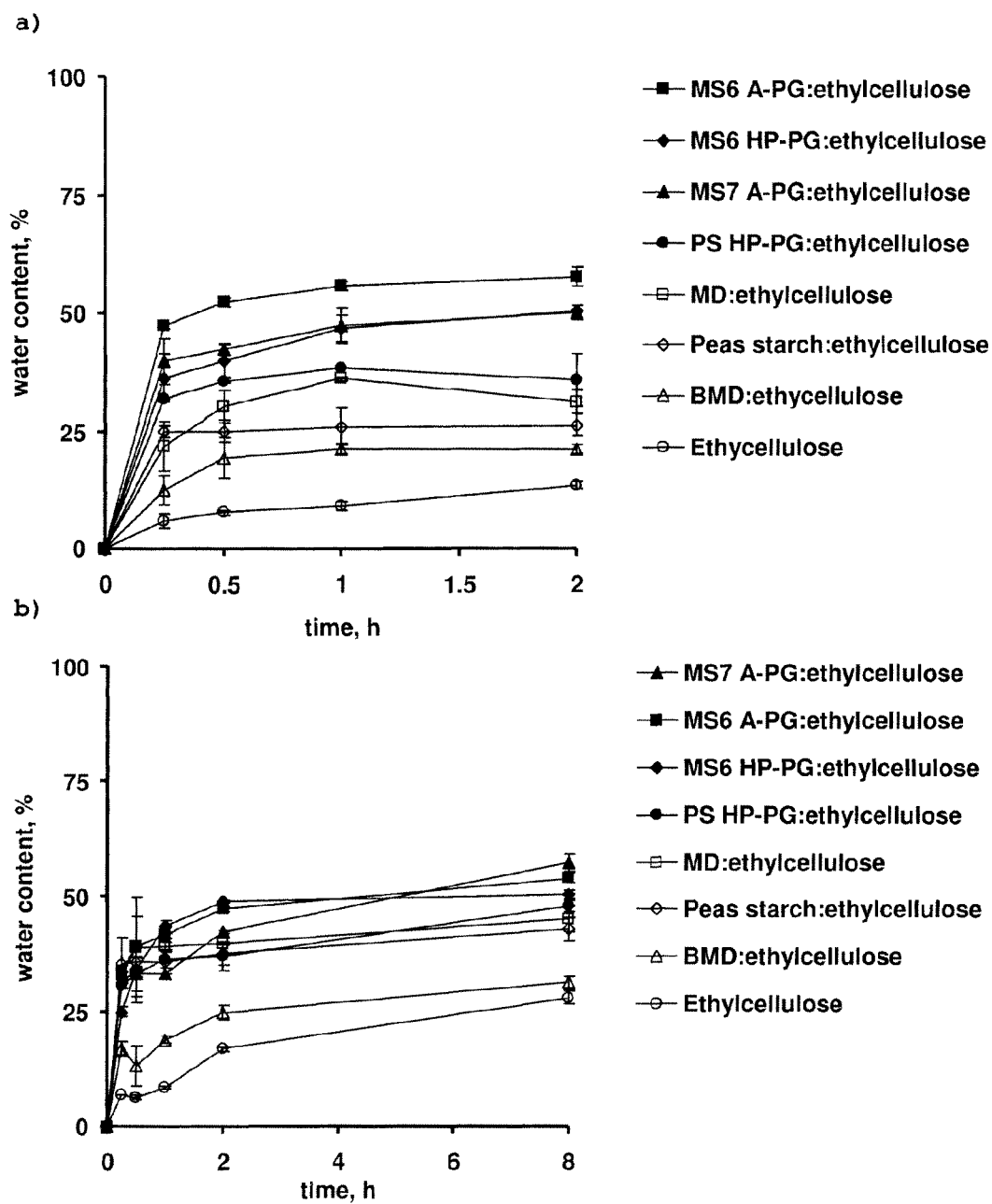
FIG. 1: Water content of thin films consisting of different types of polymer blends (indicated in the figures) upon exposure to: (a) 0.1 M HCl, and (b) phosphate buffer pH 6.8. Films consisting only of plasticized ethylcellulose are shown for reasons of comparison.

Table 1: Concentrations of bacteria [log CFU/g] in the investigated fecal samples of healthy subjects and inflammatory bowel disease patients.

Table 2: Effects of the type of polysaccharide blended with ethylcellulose and of the polysaccharide:ethylcellulose blend ratio on the mechanical properties of thin films in the dry state at room temperature.

Table 3: Dissolution media used to simulate the gradual increase in pH along the GIT.

DETAILED DESCRIPTION OF THE INVENTION

In describing and claiming the present invention, the following terminology will be used in accordance with the definitions set out herein.

As used herein, the term "active ingredient", "drug" or "pharmacologically active ingredient" or any other similar term means any chemical or biological material or compound suitable for administration by the methods previously known in the art and/or by the methods taught in the present invention, that induces a desired biological or pharmacological effect, which may include but is not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating the disease from the organism. The effect may be local, such as providing for a local anaesthetic effect, or it may be systemic.

As used herein, the term "Dysbiosis" also called dysbacteriosis is intended to mean, in the present invention, microbial imbalances as in quality and in quantity in the gastrointestinal tract. Equally the expression "colon microflora imbalance" means in the present invention, microbial imbalances as in quality and in quantity in the gastrointestinal tract especially in the colon. This phenomenon is reflected by the quality and quantity of the enzymes present in the colon. Particularly, this altered microflora is observed in the colon of patients suffering from inflammatory bowel diseases, such as Crohn's Disease (CD) and Ulcerative Colitis (UC).

As used herein, the term "controlled release delivery" or "controlled release" means that the release of the active ingredient out of the composition is controlled with respect to time or with respect to the site of delivery.

The expression "starch derivatives" means a starch that has been enzymatically or chemically treated.

The expression "modified starch" should be understood broadly, this expression refers for instance to reticulated or acetylated or hydroxypropylated or esterification starch.

The term "coat" is used herein to encompass coatings for solid supports and also capsules enclosing fluids and/or solids and the term "coated" is used similarly.

The "coating level" means the difference in weight between uncoated and coated cores that is the weight gain in percentage.

The expression "water insoluble polymer" should be understood broadly, this expression refers to polymers that do not completely dissolve in water, such as for example ethyl cellulose, certain starch derivatives or acrylic acid/methacrylic acid derivatives.

The term "indigestible water-soluble polysaccharides" as used in the present invention refers to saccharides which are not or only partially digested in the intestine by the action of acids or digestive enzymes present in the human upper digestive tract (small intestine and stomach) but which are at least partially fermented by the human intestinal flora. Indigestible water-soluble polysaccharides that may be employed in preferred embodiments of the invention are xylooligosaccharides, inulin, oligofructoses, fructo-oligosaccharides (FOS), lactulose, galactomannan and suitable hydrolysates thereof, indigestible polydextrose, indigestible dextrins and partial hydrolysates thereof, trans-galacto-oligosaccharides (GOS), xylo-oligosaccharides (XOS), acemannans, lentinans or beta-glucans and partial hydrolysates thereof, polysaccharides-K (PSK), and indigestible maltodextrins and partial hydrolysates thereof.

Polysaccharide-K is also known as polysaccharide-Krestin (PSK) in Japan, and as polysaccharide-peptide (PS-P) in China. Both have the same chemical and structural characteristics. PSK is a proteoglycan found in the polypore fungus *Trametes versicolor* and contains approximately 35% carbohydrate (91% beta-glucan), 35% protein and the remainders are free residues such as sugars, amino acids and moisture. PSK is a mixture of polysaccharides covalently linked to various peptides with an average molecular weight of 100 kilodaltons. The polysaccharide component is in a class of beta-glucans which comprise of glucopyranose units. Structural analysis showed that PSK has a 1,4-glucan configuration as the main glucoside portion with branches at positions and 6 at a frequency of one branch per several residual groups of 1-4 bonds.

As used herein, the term "cereal" is intended to mean, in the present invention, any plant belonging to the Gramineae, preferably wheat, rice, rye, oats, barley, corn, sorghum and millets.

The term "legume" is intended to mean, in the present invention, any plant belonging to the Caesalpinaceae, Mimosaceae or Papilionaceae families and in particular any plant belonging to the Papilionaceae family, such as, for example, pea, bean, broad bean, horse bean, lentil, alfalfa, clover or lupin.

This definition includes in particular all the plants described in any one of the tables present in the paper by R. Hoover et al. entitled "Composition, Structure, Functionality and Chemical Modification of Legume Starches: A Review".

The term "pea" in this instance is considered in its broadest sense and includes in particular:
all the wild varieties of smooth pea and
all the mutant varieties of smooth pea and of wrinkled pea, this being the case whatever the uses for which said varieties are generally intended (food for man, animal nutrition and/or other uses).

Said mutant varieties are in particular those referred to as "mutants r", "mutants rb", "mutants rug 3", mutants rug 4", "mutants rug 5" and "mutants lam" as described in the paper by C-L Heydley et al. entitled "Developing Novel Pea Starches", Proceedings of the Symposium of the Industrial Biochemistry and Biotechnology Group of the Biochemical Society, 1996, pp. 77-87.

The term "legume starch" is understood to mean any composition extracted, this being the case in whatever way, from a legume as defined hereinabove and having a starch content of greater than 40%, preferably of greater than 50% and more preferably still of greater than 75%, these percentages being expressed in dry weight with respect to the dry weight of said composition.

Furthermore, it is possible to use starches naturally exhibiting an amylose content within the range selected according to the invention. In particular, the starch resulting from legumes may be suitable. In accordance with the present invention, this legume starch exhibits an amylose content of less than 45%, more specifically of between 25 and 45%, preferably of between 30 and 44%, and more preferably still of between 35 and 40%.

For the purpose of the invention, the term "ingestible maltodextrin" mean maltodextrin containing indigestible glucosidic linkages conferring on those maltodextrins additional properties identical to dietetic fibers such as "branched maltodextrins". As used herein, the term "branched maltodextrins" is intended to mean the ingestible maltodextrins described in patent EP 1 006 128, of which the applicant company is the proprietor.

According to a preferred variant, said branched maltodextrins have a reducing sugar content of between 2% and 5%, and a number-average molecular mass Mn of between 2000 and 3000 g/mol.

The branched maltodextrins have a total fiber content of greater than or equal to 50% on a dry basis, determined according to AOAC method No. 2001-03 (2001).

The invention provides novel polymeric film coatings for colon targeting which are adapted to the disease state of the patients suffering from inflammatory bowel diseases.

Novel polymeric films according to the invention serve as substrates for colonic bacteria for healthy patients as for patients suffering from inflammatory bowel diseases and are likely to exhibit beneficial effects on the ecosystem of the GIT of the patients. The polymeric film is specially adapted to the conditions at the target site, also in the disease state and able to deliver pharmacologically active ingredients specifically to the colon.

In the following, the invention will be illustrated by means of the following examples as well as the figures.

Example 1

A. Materials and Methods

A.1. Materials

Branched maltodextrin (BMD) [a branched maltodextrin with non digestible glycoside linkages: α-1,2 and α-1,3, NUTRIOSE® FB 06 Roquette Frères], Pea starch (pea starch N-735), a pregelatinized hydroxypropyl pea starch (PS HP-PG)(LYCOAT® RS 780), a maltodextrin (MD)(GLUCIDEX® 1, Roquette Frères), EURYLON® 7 A-PG (an acetylated and pregelatinized high amylose maize starch (70% amylose) (Roquette Freres, Lestrem, France), EURYLON® 6 A-PG (an acetylated and pregelatinized high amylose maize starch) (60% amylose) (Roquette Freres, Lestrem, France) and EURYLON® 6 HP-PG (a hydroxypropylated and pregelatinized high amylose maize starch (60% amylose) (Roquette Freres, Lestrem, France); aqueous ethylcellulose dispersion (Aquacoat® ECD 30; FMC Biopolymer, Philadelphia, USA); triethylcitrate (TEC; Morflex®, Greensboro, USA); pancreatin (from mammalian pancreas=mixture containing amylase, protease and lipase; Fisher Bioblock, Illkirch, France); extract from rat intestine (rat intestinal powder, containing amylase, sucrase, isomaltase and glucosidase; Sigma-Aldrich, Isle d'Abeau Chesnes, France); Columbia blood agar, extracts from beef and yeast as well as tryptone (=pancreatic digest of casein) (Becton Dickinson, Sparks, USA); L-cysteine hydrochloride hydrate (Acros Organics, Geel, Belgium); McConkey agar (BioMerieux, Balme-les-Grottes, France); cysteinated Ringer solution (Merck, Darmstadt, Germany).

A.2. Film Preparation

Thin polymeric films were prepared by casting blends of different types of aqueous polysaccharides and aqueous ethylcellulose dispersion into Teflon moulds and subsequent drying for 1 d at 60° C. The water soluble polysaccharide was dissolved in purified water (5% w/w) and blended with plasticized ethylcellulose dispersion (25% TEC, overnight stirring; 15% w/w polymer content) at a ratio of 1:3 (polymer:polymer w:w). The mixture was stirred for 6 h prior to casting.

A.3. Film Characterization

The thickness of the films was measured using a thickness gauge (Minitest 600; Erichsen, Hemer, Germany). The mean thickness of all films was in the range of 300-340 µm. The water uptake and dry mass loss kinetics were measured gravimetrically upon exposure to:

(i) simulated gastric fluid (0.1 M HCl)
(ii) simulated intestinal fluid [phosphate buffer pH 6.8 (USP 30) with or without 1% pancreatin or 0.75% extract from rat intestine]
(iii) culture medium inoculated with feces from healthy subjects
(iv) culture medium inoculated with feces from inflammatory bowel disease patients
(v) culture medium free of feces for reasons of comparison.

Culture medium was prepared by dissolving 1.5 g beef extract, 3 g yeast extract, 5 g tryptone, 2.5 g NaCl and 0.3 g L-cysteine hydrochloride hydrate in 1 L distilled water (pH 7.0±0.2) and subsequent sterilization in an autoclave. Feces of patients with Crohn's Disease or Ulcerative Colitis as well as feces of healthy subjects were diluted 1:200 with cysteinated Ringer solution; 2.5 mL of this suspension was diluted with culture medium to 100 mL. Film pieces of 1.5×5 cm were placed into 120 mL glass containers filled with 100 mL pre-heated medium, followed by horizontal shaking at 37° C. (GFL 3033, Gesellschaft für Labortechnik, Burgwedel, Germany). The incubation with fecal samples was performed under anaerobic conditions (5% CO2, 10% H2, 85% N2). At predetermined time points samples were withdrawn, excess water removed, the films accurately weighed (wet mass) and dried to constant weight at 60° C. (dry mass). The water content (%) and dry film mass (%) at time t were calculated as follows:

$$\text{water content (\%) }(t) = \frac{\text{wet mass }(t) - \text{dry mass }(t)}{\text{wet mass }(t)} \cdot 100\% \quad (1)$$

$$\text{dry film mass (\%) }(t) = \frac{\text{dry mass }(t)}{\text{dry mass }(t=0)} \cdot 100\% \quad (2)$$

A.4. Bacteriological Analysis

For the bacteriological analysis of fecal samples, the latter were diluted 1:10 with cysteinated Ringer solution. Eight further tenfold dilutions in cysteinated Ringer solution were prepared and 0.1 mL of each dilution was plated onto non-selective, modified Columbia blood agar (for total cultivable counts) and on McConkey agar (being selective for enterobacteria). Columbia blood agar plates were incubated during 1 week at 37° C. under anaerobic conditions (5% CO2, 10% H2, 85% N2). Colonies were outnumbered, predominant colonies subcultured and identified based on phenotypic identification criteria. 25 McConkey agar plates were incubated during 48 h at 37° C. in air. The colonies were outnumbered and identified using the API 20E system (BioMerieux, Balme-les-Grottes, France). Counts were expressed as log CFU/g (Colony Forming Units per gram) of fresh feces.

For the bacteriological analysis of the microflora developed upon film incubation with fecal samples, photomicrographs were taken after Gram-staining with an Axiostar plus microscope (Carl Zeiss, Jena, Germany), equipped with a camera (Unit DS-L2, DS camera Head DS-Fi 1; Nikon, Tokyo, Japan). Incubation was performed in a glucides-free culture medium containing only small amounts of polypeptides (thus, favoring the use of the investigated polysaccharides as substrates) under anaerobic conditions.

B. Results and Discussion

B.1. Film Properties in the Upper GIT

The permeability of a polymeric system for a drug strongly depends on its water content and dry mass, which determine the density and mobility of the macromolecules. For instance, in dry hydroxypropyl methylcellulose (HPMC)-based matrix tablets the apparent diffusion coefficient of a drug approaches zero, whereas in a completely hydrated HPMC gel diffusivities can be reached, which are in the same order of magnitude as in aqueous solutions. With increasing water content the macromolecular mobility significantly increases and, thus, the free volume available for diffusion. In some systems, the polymer undergoes a glassy-to-rubbery phase transition as soon as a critical water content is reached. This leads to a significant, stepwise increase in polymer and drug mobility. Thus, the water content of a polymeric film coating can give important insight into the macromolecular mobility and, hence, permeability for a drug. FIGS. 1a and 1b show the water uptake kinetics of thin films consisting of various types of polysaccharide:ethylcellulose blends in 0.1 N HCl and phosphate buffer pH 6.8, respectively. The presence of ethylcellulose in all films allows avoiding premature dissolution in the upper GIT. The investigated polysaccharides are all water-soluble and aim at providing the sensitivity of the coatings' drug permeability to the surrounding environment: Once the colon is reached, the polysaccharides are to be enzymatically degraded and drug release to be started. The polysaccharide:ethylcellulose blend ratio in FIG. 1 is constant: 1:3. Clearly, the water uptake rates and extents significantly depend on the type of polysaccharide. The ideal film coating allowing for colon targeting should take up only small amounts of water at a low rate in both media in order to prevent premature drug release in the upper GIT. As it can be seen, blends of ethylcellulose and BMD or peas starch are most promising for this purpose. Plasticized ethylcellulose films without water-soluble polysaccharide take up only minor amounts of water (empty circles).

In addition to the water uptake kinetics also the dry mass loss behaviour of thin polymeric films serves as an indicator for the coatings' permeability for the drug, and, hence, potential to suppress premature release within the upper GIT. If the films loose significant amounts of dry mass upon exposure to the release media, the coatings can be expected to become permeable for many drugs, in particular those with a low molecular weight such as 5-aminosalicylic acid (5-ASA, 153.1 Da). FIGS. 2a and 2b illustrate the experimentally determined dry mass loss of thin films consisting of various polysaccharide:ethylcellulose blends (constant ratio=1:3) upon exposure to 0.1 N HCl and phosphate buffer pH 6.8, respectively. The ideal film looses only minor amounts of dry mass at a low rate (or no mass at all), assuring dense polymeric networks which are poorly permeable for the incorporated drug under these conditions. As it can be seen, the dry mass loss of peas starch- and BMD-containing films is very low, even after up to 8 h exposure to these release media. The observed decrease in dry mass can at least partially be attributed to the leaching of the water-soluble plasticizer triethyl citrate (TEC, used to plasticize the aqueous ethylcellulose dispersion) into the bulk fluid. In addition, parts of the water-soluble polysaccharides might leach out of the films. Plasticized ethylcellulose films without water-soluble polysaccharide loose only very small amounts of water, irrespective of the type of release medium (empty circles). However, the permeability of intact ethylcellulose films is known to be very low for many drugs, which can at least partially be attributed to the low water-uptake rates and extents of these systems. For this reason, intact ethylcellulose films are also used as moisture protective coatings. Please note that the loss of the water-soluble plasticizer TEC into the bulk fluids can be expected to be much more pronounced in films containing 25% (w/w) water-soluble polysaccharides compared to pure (plasticized) ethylcellulose films, because the increased water uptake rates and extents (FIG. 1) of the blended systems lead to much higher polymer chain mobility and, thus, also increased TEC mobility.

Figure 2:
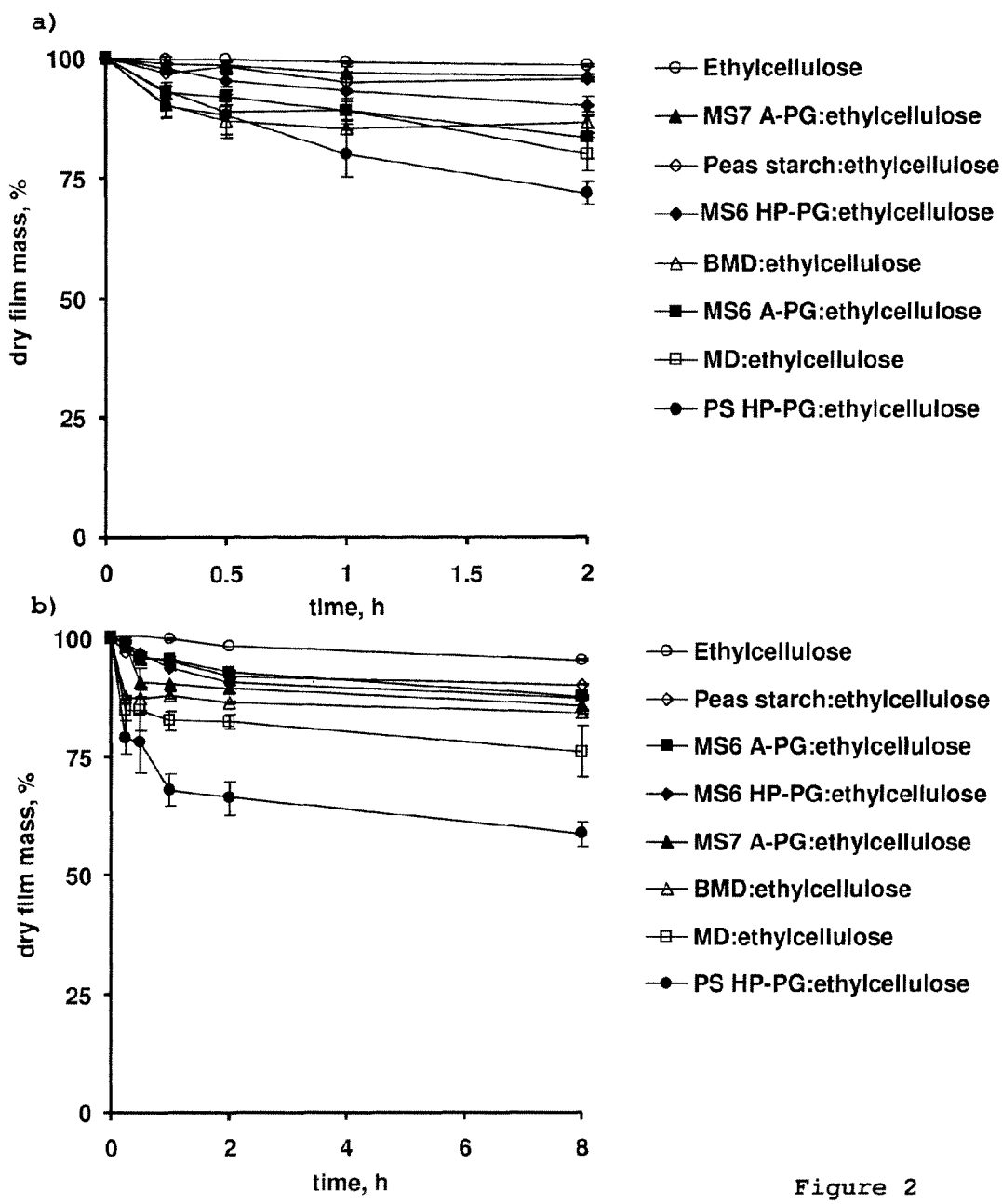
FIG. 2: Dry mass of thin films consisting of different types of polymer blends (indicated in the figures) upon exposure to: (a) 0.1 M HCl, and (b) phosphate buffer pH 6.8. Films consisting only of plasticized ethylcellulose are shown for reasons of comparison.
Figure 3:
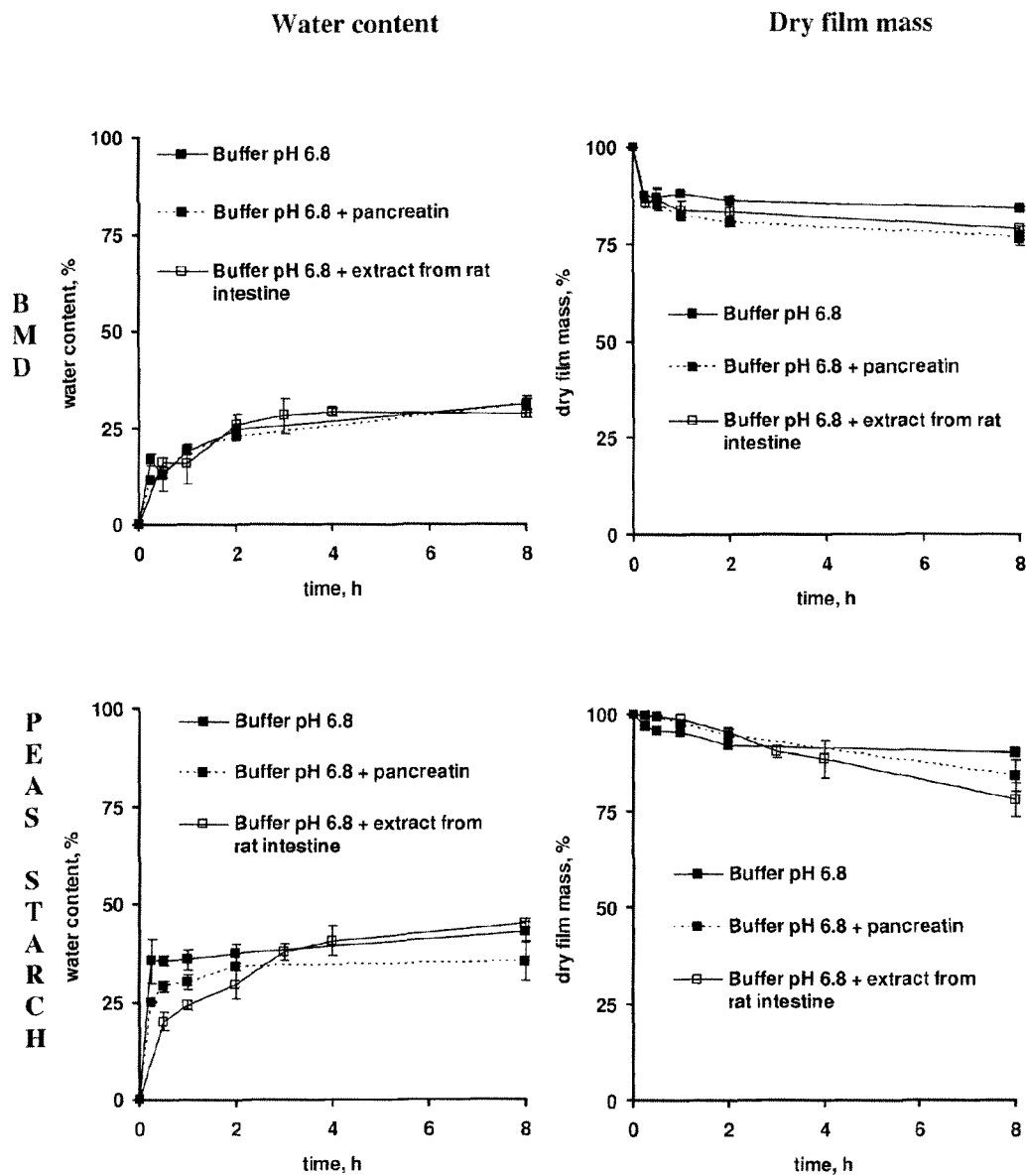
FIG. 3: Water content and dry mass of thin films consisting of branched maltodextrin or peas starch blended with ethylcellulose upon exposure to phosphate buffer pH 6.8 containing or not pancreatin or extract from rat intestine.

It has to be pointed out that the results shown in FIG. 2 were obtained in the absence of any enzymes. It is well known that pancreatic enzymes can degrade certain polysaccharides and, thus, potentially induce significant mass loss and water uptake under in vivo conditions, resulting in increased film permeability for the drug. To clarify the importance of this phenomenon, the water uptake kinetics and dry mass loss behaviour of the thin films were also measured in the presence of pancreatin (=mixture containing amylase, protease and lipase) and of an extract from rat intestine (containing amylase, sucrase, isomaltase and glucosidase) in phosphate buffer pH 6.8 (FIG. 3). Clearly, the addition of these enzymes did not significantly affect the resulting water uptake and dry mass loss kinetics of the investigated films. Thus, the latter do not serve as substrates for these enzymes.

B.2. Film Properties in the Colon

Figure 4:
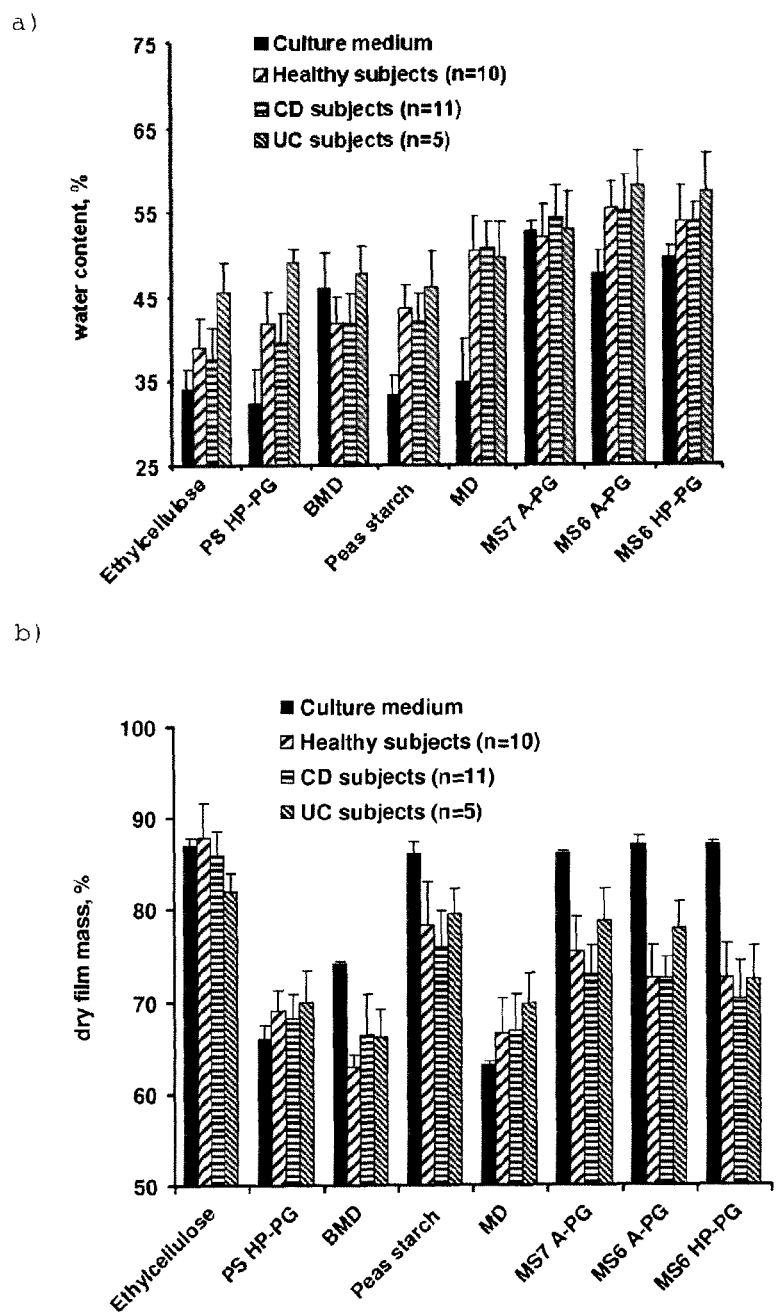
FIG. 4: Water content and dry mass of thin films consisting of different types of polysaccharides blended with ethylcellulose upon exposure to culture medium, culture medium inoculated with feces of healthy subjects and culture medium inoculated with feces of Crohn's Disease (CD) patients and Ulcerative Colitis (UC) patients (as indicated in the figures). Films consisting only of plasticized ethylcellulose are shown for reasons of comparison.

Once the colon is reached, the polymeric film coatings should become permeable for the drug. This can for instance be induced by (partial) enzymatic degradation. Importantly, the concentrations of certain enzymes are much higher in the colon than in the upper GIT. This includes enzymes, which are produced by the natural microflora of the colon (this part of the GIT contains much more bacteria than the stomach and small intestine). However, great caution must be paid when using this type of colon targeting approach, because the microflora of patients suffering from inflammatory bowel diseases can be significantly different from the microflora of healthy subjects. Thus, the drug delivery system must be adapted to the disease state of the patient. Table 1 shows for instance the concentrations of the bacteria determined in the fecal samples of the healthy subjects as well as of the Crohn's Disease and Ulcerative Colitis patients included in this study. Importantly, there were significant differences, in particular with respect to the concentrations of *Bifidobacterium* (being able to degrade complex polysaccharides due to multiple extracellular glycosidases) and *Escherichia coli*, which where present at much higher concentrations in the feces of healthy subjects compared to the feces of the inflammatory bowel disease patients. In contrast, the fecal samples of the Crohn's Disease and Ulcerative Colitis patients contained lactose negative *E. coli, Citrobacter freundii, Klebsiella pneumoniae, Klebsiella oxytoca* and *Enterobacter cloacae*, which were not detected in healthy subjects. Thus, there are fundamental differences in the quality and quantity of the microflora, which must be taken into account: Polymeric film coatings, which allow for colon targeting under physiological conditions in a healthy volunteer, might fail under the pathophysiological conditions in the disease state of a patient. To address this very crucial point, which is very often neglected, the water uptake and dry mass loss of thin films consisting of various types of polysaccharide:ethylcellulose blends were determined upon exposure to fecal samples from Crohn's Disease and Ulcerative Colitis patients as well as to the feces of healthy subjects and to pure culture medium for reasons of comparison (FIG. 4). Appropriate films should take up considerable amounts of water and show significant dry mass loss upon exposure to patients' feces in order to induce drug release at the site of inflammation in the colon. As it can be seen in FIGS. 4a and 4b, films based on ethylcellulose: BMD and ethylcellulose: peas starch (which are the two most promising types of polymer blends based on the above described results obtained in media simulating the contents of the upper GIT) show significant water uptake and dry mass loss upon exposure to the feces of Crohn's Disease patients, Ulcerative Colitis patients as well as of healthy subjects. Please note that also other types of polymer blends look promising with respect to the presented films' water uptake and dry mass loss behaviour upon exposure to fecal samples (or even more appropriate than ethylcellulose: BMD and ethylcellulose: peas starch blends). However, these systems already take up considerable amounts of water and remarkably loose in dry mass upon contact with media simulating the contents of the upper GIT (FIGS. 1 and 2).

Figure 5:
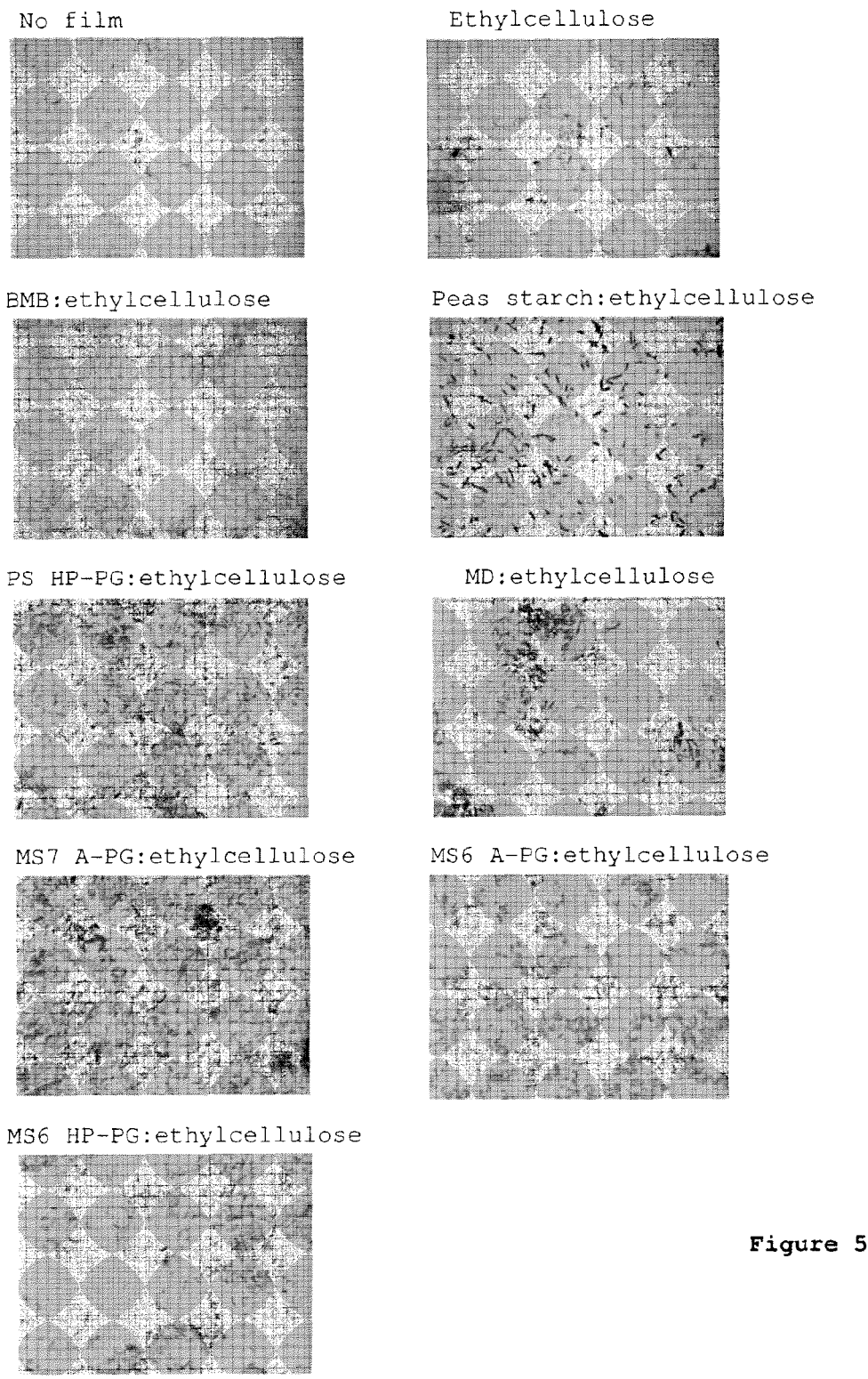
FIG. 5: Pictures of the microflora developed upon incubation of thin, polymeric films of different composition (indicated in the figure) with fecal samples of inflammatory bowel disease patients.

The fact that the investigated polymeric films serve as substrates for the bacteria in feces from inflammatory bowel disease patients could be further confirmed by the analysis of the microflora developed upon film exposure to fecal samples under anaerobic conditions at 37° C. (FIG. 5). Clearly, specific types of bacteria proliferated upon incubation with the blended films. Importantly, this phenomenon can be expected to be highly beneficial for the ecosystem of the GIT of the patients in the disease state, normalizing the microflora in the colon. This very positive, pre-biotic effect comes in addition to the drug targeting effect. Biological samples incubated without any polymeric films or with pure (plasticized) ethylcellulose films showed much less bacterial growth (FIG. 5).

The novel polymeric film coatings identified for colon targeting are composed of water insoluble polymer: polysaccharides particularly ethylcellulose: BMD, ethylcellulose: pea starch, ethylcellulose: MD, ethylcellulose: EURYLON® 6 A-PG, ethylcellulose: EURYLON® 6 HP-PG and ethylcellulose: EURYLON® 7 A-PG blends, which are adapted to the disease state of the patients. Importantly, low water uptake and dry mass loss rates and extents in media simulating the contents of the upper GIT can be combined with elevated water uptake and dry weight loss upon contact with feces from inflammatory bowel disease patients. Changes in the composition of the flora in the colon of patients indicate that these polysaccharides serve as substrates for colonic bacteria in the disease state and are likely to exhibit beneficial effects on the ecosystem of the GIT of the patients. The obtained new knowledge, thus, provides the basis for the development of novel polymeric film coatings able to deliver drugs specifically to the colon. Importantly, these polymeric barriers are adapted to the conditions at the target site in the disease state.

Example 2

A. Materials and Methods

A.1. Materials

Branched maltodextrin (BMD) (a water-soluble, branched maltodextrin with high fiber contents obtained from wheat starch; NUTRIOSE® FB 06, Roquette Freres, Lestrem, France); a maltodextrin (GLUCIDEX® 1, Roquette Frères); aqueous ethylcellulose dispersion (Aquacoat ECD 30; FMC Biopolymer, Philadelphia, USA); triethylcitrate (TEC; Morflex, Greensboro, USA).

A.2. Preparation of Thin, Polymeric Films

Thin polymeric films were prepared by casting blends of different types of polysaccharides and aqueous ethylcellulose dispersion into Teflon moulds and subsequent drying for 1 d at 60° C. The water soluble polysaccharide was dissolved in purified water, blended with plasticized aqueous ethylcellulose dispersion (25.0, 27.5 or 30.0% w/w TEC, referred to the ethylcellulose content overnight stirring; 15% w/w polymer content) at a ratio of 1:2, 1:3, 1:4, 1:5 (polymer:polymer w:w), as indicated. The mixtures were stirred for 6 h prior to casting.

A.3. Film Characterization

The thickness of the films was measured using a thickness gauge (Minitest 600; Erichsen, Hemer, Germany). The mean thickness of all films was in the range of 300-340 µm. The water uptake and dry mass loss kinetics of the films were measured gravimetrically upon exposure to 0.1 M HCl and phosphate buffer pH 6.8 (USP 30) as follows: Pieces of 1.5×5 cm were placed into 120 mL plastic containers filled with 100 mL pre-heated medium, followed by horizontal shaking at 37° C. (80 rpm, GFL 3033; Gesellschaft fuer Labortechnik, Burgwedel, Germany). At predetermined time points samples were withdrawn, excess water removed, the films accurately weighed (wet mass) and dried to constant weight at 60° C. (dry mass). The water content (%) and dry film mass (%) at time t were calculated as follows:

$$\text{Water content (\%) } (t) = \frac{\text{wet mass } (t) - \text{dry mass } (t)}{\text{wet mass } (t)} \cdot 100\% \quad (1)$$

$$\text{Dry film mass (\%) } (t) = \frac{\text{dry mass } (t)}{\text{dry mass } (t=0)} \cdot 100\% \quad (2)$$

A.4. Mechanical Properties of Thin Films

The mechanical properties of the films in the dry and wet state were determined with a texture analyzer (TAXT.Plus, Winopal Forschungsbedarf, Ahnsbeck, Germany) and the puncture test. Film specimens were mounted on a film holder (n=6). The puncture probe (spherical end: 5 mm diameter) was fixed on the load cell (5 kg), and driven downward with a cross-head speed of 0.1 mm/s to the center of the film holder's hole. Load versus displacement curves were recorded until rupture of the film and used to determine the mechanical properties as follows:

$$\text{Puncture strength} = \frac{F}{A} \quad (3)$$

Where F is the load required to puncture the film and A the cross-sectional area of the edge of the film located in the path.

$$\% \text{ elongationat break} = \frac{\sqrt{R^2 + D^2} - R}{R} \cdot 100\% \quad (4)$$

Here, R denotes the radius of the film exposed in the cylindrical hole of the holder and D the displacement.

$$\text{Energy at break unit volume} = \frac{AUC}{V} \quad (5)$$

Where AUC is the area under the load versus displacement curve and V the volume of the film located in the die cavity of the film holder.

B. Results and Discussion

B.1. BMD:Ethylcellulose Blends a) Water Uptake and Dry Mass Loss of Thin Films

The permeability of a polymeric film coating strongly depends on its water content. In a dry system, the diffusion coefficients approach zero. With increasing water content, the mobility of the macromolecules increases and, thus, also the mobility of incorporated drug molecules. FIGS. 6a and 6b show the gravimetrically measured water uptake of thin, polymeric films based on different BMD:ethylcellulose blends upon exposure to 0.1 M HCl and phosphate buffer pH 6.8 at 37° C. Clearly, the polymer blend ratio significantly affected the resulting water penetration rates and extents. With increasing BMD content the amount of water taken up as well as the rate of this mass transport step increased. This phenomenon can be attributed to the more hydrophobic nature of ethylcellulose compared to the water-soluble polysaccharides BMD. Thus, it can be expected that the mobility of a drug within this type of polymeric films significantly increases with increasing BMD contents. Interestingly, the water uptake rates and extents of the investigated films were higher in phosphate buffer pH 6.8 than in 0.1 N HCl (FIG. 6b versus FIG. 6a). This can be attributed to the presence of the emulsifier sodium dodecyl sulfate (SDS) in the aqueous ethylcellulose dispersion Aquacoat ECD. At low pH, SDS is protonated and neutral, whereas at pH 6.8 it is deprotonated and negatively charged. Thus, the ability to decrease interfacial surface tensions is more pronounced at pH 6.8, resulting in facilitated water penetration into the system. Importantly, even the highest water uptake rates and extents of the investigated systems (up to a blend ratio of 1:2 BMD: ethylcellulose) are relatively low (FIG. 6). Thus, premature drug release within the upper GIT can be expected to be limited with this type of polymeric films, irrespective of the polymer:polymer blend ratio in the investigated range.

In addition to the water uptake kinetics, also the dry mass loss behaviour of thin polymeric films offers important insight into the latter's ability to suppress or allow drug release. The effects of the BMD:ethylcellulose blend ratio on the resulting dry mass loss of thin films upon exposure to 0.1 M HCl and phosphate buffer pH 6.8 are illustrated in FIGS. 7a and 7b, respectively. Clearly, both, the rate and the extent of the dry mass loss increased with increasing BMD contents. This can at least partially be attributed to the leaching of this water-soluble compound out into the bulk fluids. However, also the diffusion of the water-soluble plasticizer TEC (which is used to facilitate the fusion of the ethylcellulose nanoparticles during film formation) into the release media can be expected to be significantly facilitated: Due to the increasing water contents of the systems (FIG. 6), the mobility of the polymer chains increases and, thus, also the mobility of the low molecular weight plasticizer. Please note that the dry mass loss of pure (plasticized) ethylcellulose films can primarily be attributed to such TEC leaching and that a (slight)

pH dependence of this phenomenon is observed (due to the SDS effect discussed above). Importantly, the dry mass loss is limited in all cases, and the presence of the water-insoluble ethylcellulose in the films effectively hinders the leaching of the water-soluble polysaccharides into the bulk fluids. Again, premature drug release within the upper parts of the GIT is likely to be limited, irrespective of the polymer:polymer blend ratio in the investigated range (up to 1:2 BMD: ethylcellulose).

b) Mechanical Properties of Thin Films

In addition to limited water uptake and dry mass loss in the upper GIT, a polymeric film coating providing site-specific drug delivery to the colon must be sufficiently (mechanically) stable in order to avoid accidental crack formation due to the shear stress encountered in the stomach and small intestine in vivo. In addition, significant hydrostatic pressure might be built up within a coated dosage form due to the penetration of water into the system upon contact with aqueous body fluids. The presence/absence of osmotically active drugs and/or excipients in the core formulation can strongly affect the importance of this phenomenon. Fragile film coatings are likely to rupture because of such shear forces from outside (caused by the motility of the GIT) and hydrostatic pressures from inside (caused by water penetration) they are exposed to. In order to be able to estimate the risk of such accidental crack formation, the energy required to break the investigated BMD:ethylcellulose films was measured using a texture analyzer and the puncture test before and upon exposure to 0.1 N HCl and phosphate buffer pH 6.8, respectively. The white bars in FIG. 8 indicate the mechanical stability of thin BMD: ethylcellulose films (plasticized with 25% w/w TEC, referred to the ethylcellulose content) in the dry state at room temperature as a function of the polymer blend ratio. Clearly, the energy at break of the films significantly increased with increasing ethylcellulose content, indicating that this compound mainly contributes to the mechanical stability of the system under these conditions. Importantly, all the investigated films showed a mechanical stability that is likely to be sufficient to withstand the shear stress and hydrostatic pressure they are exposed to within the upper GIT at appropriate coating levels. This was confirmed by the experimentally determined puncture strength and % elongation at break of the films (data not shown). However, it must be pointed out that the penetration of water into the polymeric systems significantly changes the composition of the films (FIGS. 6 and 7) and, thus, their mechanical properties. In particular the fact that water acts as a plasticizer for many polymers and that the water-soluble TEC and polysaccharides (at least partially) leach out of the polymeric networks can be expected to lead to time-dependent changes in the mechanical stability of the films. In addition, the results shown in FIG. 8 were obtained at room temperature, and not at 37° C. body temperature. It is well known that the temperature of a polymeric network can strongly affect its mechanical properties, e.g. due to glassy-to-rubbery phase transitions.

For these reasons the energy required to break the investigated BMD:ethylcellulose films was also measured upon exposure to 0.1 N HCl for up to 2 h and upon exposure to phosphate buffer pH 6.8 for up to 8 h at 37° C. (FIG. 9). As it can be seen, the mechanical stability of the polymeric networks decreased with time, irrespective of the polymer blend ratio and type of release medium. This can at least partially be attributed to the leaching of the water-soluble plasticizer TEC and of the polysaccharides into the bulk fluids. Importantly, even the lowest observed values indicate that accidental crack formation due to external shear stress and/or internal hydrostatic pressure encountered in vivo is unlikely (at appropriate coating levels). Again, this was consistent with the experimentally determined puncture strength and % elongation of the films, irrespective of the polymer blend ratio, exposure time and type of release medium (data not shown).

c) Effects of the Plasticizer Content

Figure 10:
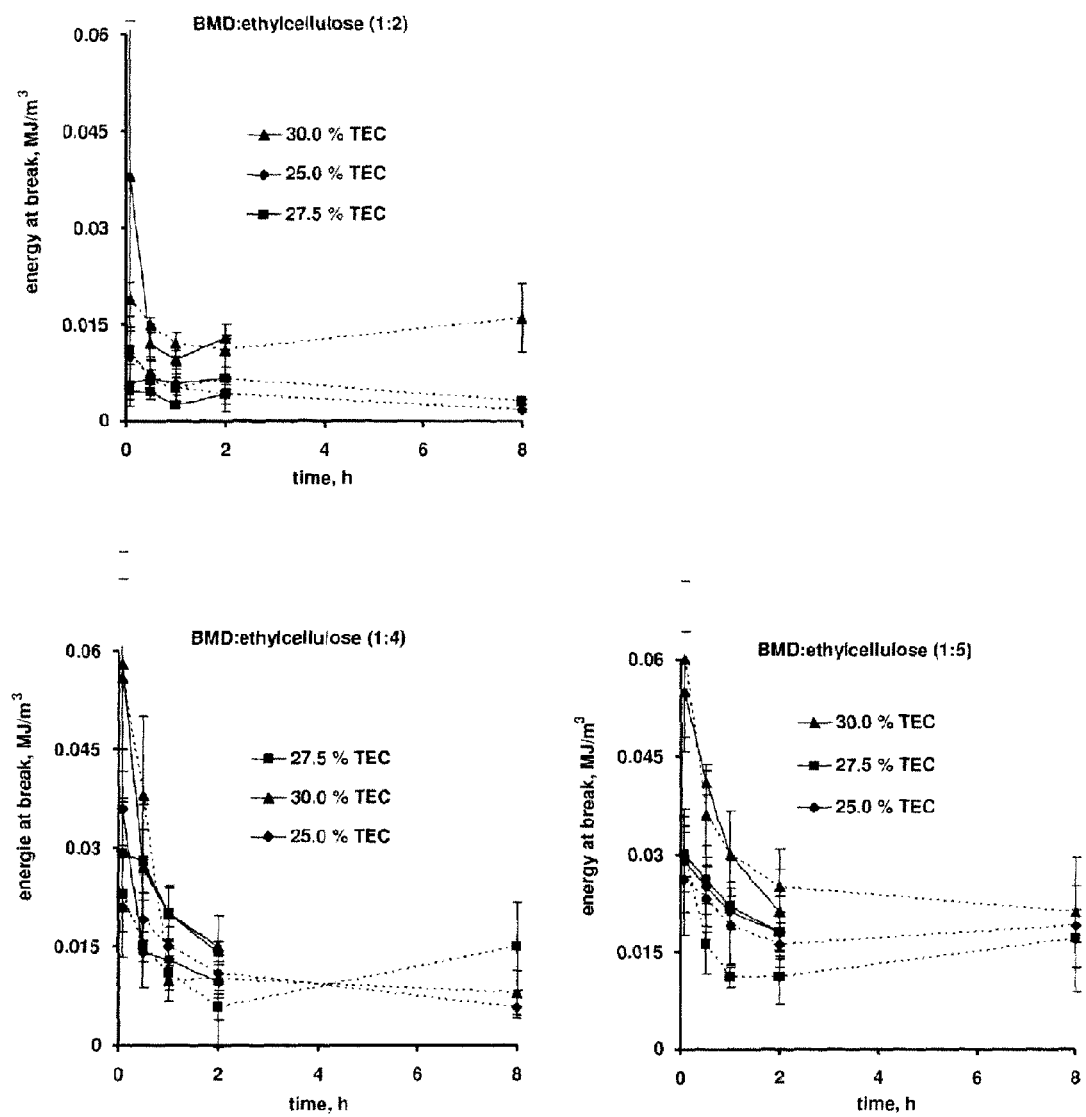
FIG. 10: Changes in the energy required to break thin films consisting of branched maltodextrin:ethylcellulose (the blend ratio is indicated on the top of figures) plasticized with different amounts of TEC (the percentages refer to the ethylcellulose mass) upon exposure to 0.1 M HCl for 2 h (solid curves) and phosphate buffer pH 6.8 for 8 h at 37° C. (dotted curves).

It is well known that the plasticizer content can significantly affect the mechanical properties of polymeric films. In order to evaluate the importance of this phenomenon for the investigated BMD:ethylcellulose blends, the percentage of incorporated TEC was increased from 25 to 30% w/w (referred to the ethylcellulose content). TEC contents below 25% w/w would render the fusion of the ethylcellulose nanoparticles during film formation difficult, the mobility of the polymer chains being crucial for this step. TEC contents higher than 30% w/w significantly increase the sticking tendency during coating and curing and should, thus, be avoided. As it can be seen in FIG. 8, the mechanical stability of the BMD:ethylcellulose films significantly increased with increasing TEC content, irrespective of the polymer blend ratio. This was consistent with the experimentally determined puncture strength and % elongation of the films (data not shown). Thus, in case of osmotically highly active core formulations (resulting in significant hydrostatic pressure built up within the dosage forms upon water penetration), the required coating levels (avoiding accidental crack formation) can be decreased by increasing the TEC content. Again, it was important to monitor the effects of the time-dependent changes in the composition of the polymeric networks upon exposure to 0.1 N HCl and phosphate buffer pH 6.8 as well as of the increase in temperature to 37° C. As it can be seen in FIG. 10, the energy required to break the films decreased upon exposure to the release media for the reasons discussed above, irrespective of the polymer blend ratio, initial plasticizer content and type of release medium. Importantly, in all cases an increase in the initial TEC content from 25 to 30% w/w (referred to the ethylcellulose content) led to increased mechanical stability at all time points.

Figure 11:
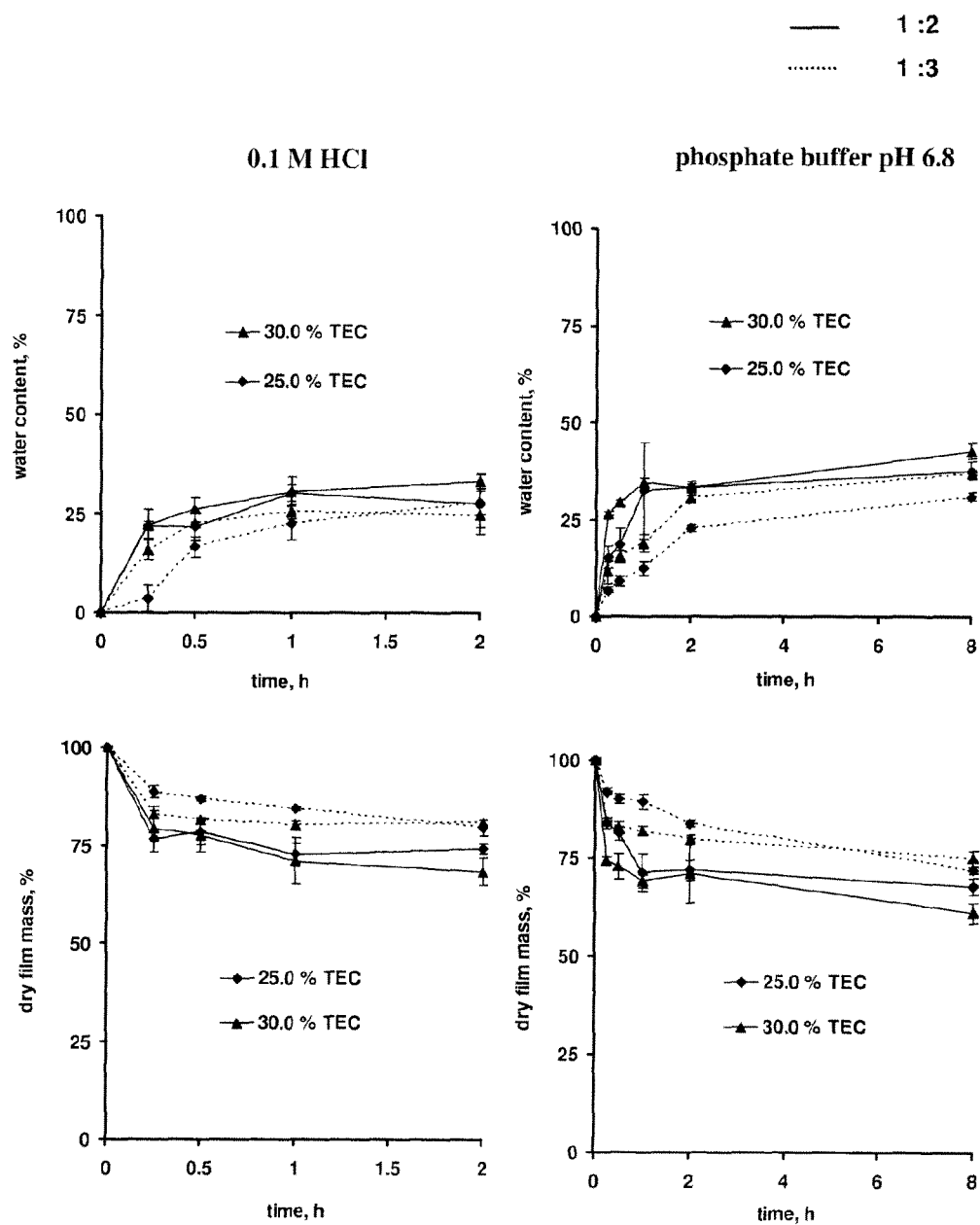
FIG. 11: Effects of the plasticizer content (indicated in the figures, referred to the ethylcellulose mass) on the water uptake and dry mass loss of branched maltodextrin:ethylcellulose films upon exposure to 0.1 M HCl and phosphate buffer pH 6.8, respectively. The solid and dotted curves represent results obtained at the blend ratios 1:2 and 1:3.

However, when increasing the percentage of the water-soluble plasticizer TEC in the polymeric films, also the rates and extents of the systems' water uptake and dry mass loss upon exposure to aqueous media can be expected to increase. This might potentially lead to significantly increased drug permeability of the polymeric films, resulting in potential premature drug release within the upper GIT. To estimate the importance of these phenomena, the water uptake and dry mass loss kinetics of the investigated films were monitored upon exposure to 0.1 N HCl for 2 h and upon exposure to phosphate buffer pH 6.8 for 8 h. The highest TEC content (30%) was selected as well as the two most critical BMD: ethylcellulose blend ratios: 1.2 and 1:3 (FIG. 11). Importantly, the resulting changes in the water uptake and dry mass loss kinetics were only minor when increasing the initial TEC content from 25 to 30%, irrespective of the polymer blend ratio and type of release medium. Thus, the mechanical stability of BMD: ethylcellulose films can efficiently be improved by increasing the plasticizer level, without loosing the systems' capability to suppress drug release within the upper GIT.

BMD:ethylcellulose blends are film coating materials for advanced drug delivery systems allowing for colon targeting. Importantly, desired system properties, being adapted to the specific needs of a particular treatment (e.g., osmotic activity and dose of the drug) can easily be adjusted by varying the polymer:polymer blend ratio up to 1:2, preferentially between 1:2 and 1:8 further preferentially 1:3 to 1:6, see 1:4 to 1:5, as well as the plasticizer content between 25% to 30% w/w referred to the water insoluble polymer content.

B.2. MD: Ethylcellulose Blends

We have shown in previous examples that blends of ethylcellulose and different types of polysaccharides in particular MD (unbranched maltodextrin) allow for site specific drug delivery to the colon in order to improve the local treatment of inflammatory bowel diseases. Importantly, such films serve as substrates for the microflora in the disease state of patients suffering from Crohn's Diseases and Ulcerative Colitis. However, it is yet unclear in how far the polymer:polymer blend ratio can affect the resulting systems' properties, in particular their water uptake and dry mass loss kinetics as well as their mechanical resistance to internal and external stress exhibited in vivo.

Figure 12:
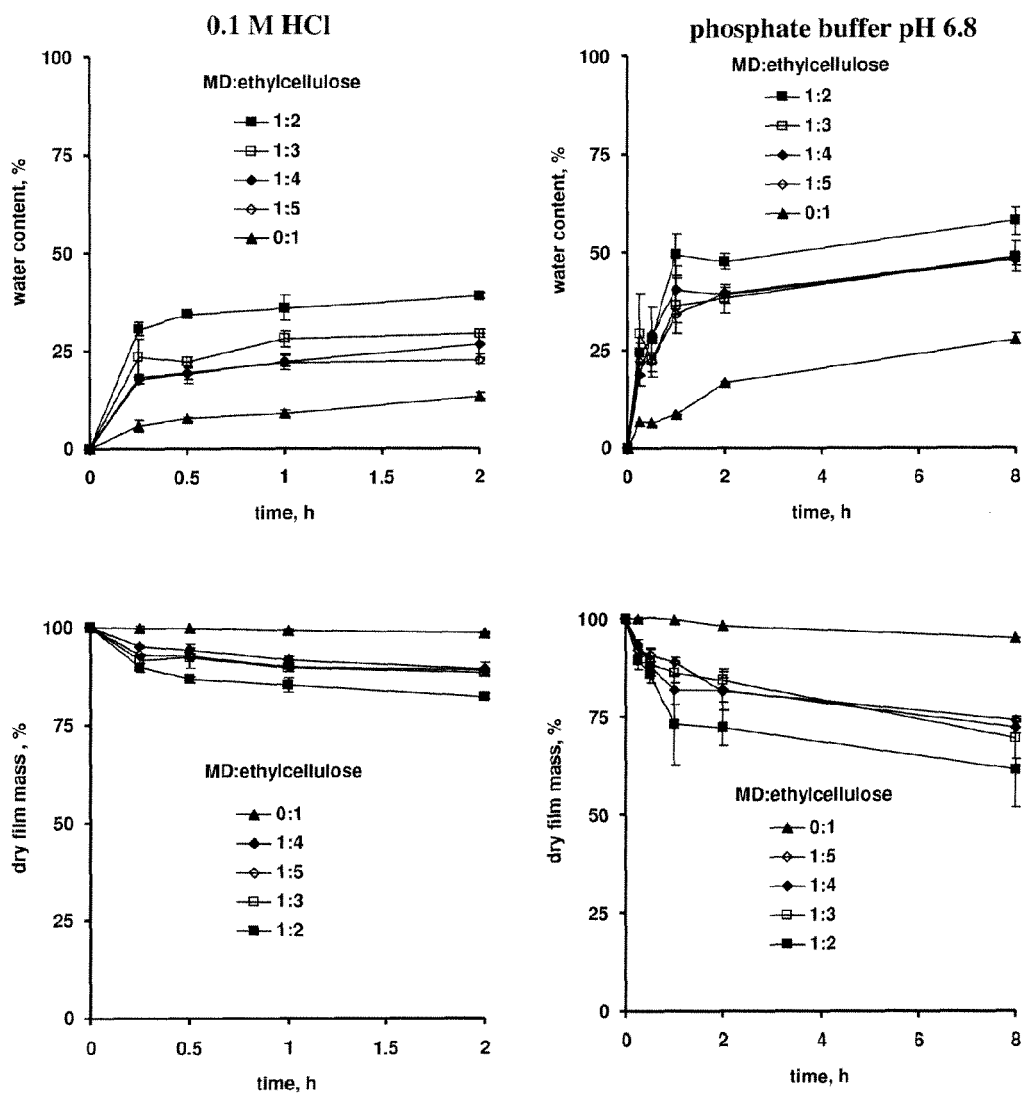
FIG. 12: Water uptake and dry mass loss of thin films consisting of maltodextrin:ethylcellulose blends upon exposure to 0.1 M HCl and phosphate buffer pH 6.8, respectively. The polymer blend ratio is indicated in the figures. For reasons of comparison also the behaviour of pure (plasticized) ethylcellulose films is shown.

FIG. 12 shows the effects of the composition of MD:ethylcellulose films on the resulting water uptake kinetics and dry mass loss behaviour upon exposure to 0.1 M HCl and phosphate buffer pH 6.8, respectively. For reasons of comparison also the results obtained with pure (plasticized) ethylcellulose films are shown. Clearly, the water uptake rates and extents significantly increased when increasing the MD:ethylcellulose blend ratio from 1:5 to 1:2. This can be attributed to the fact that MD is a maltodextrin and much more hydrophilic than ethylcellulose. At high initial MD contents the water content became significant, e.g. about half of the films consisted of water in the case of 1:2 blends after 1 h exposure to phosphate buffer pH 6.8. This can be expected to render an efficient suppression of the release of freely water-soluble, low molecular weight drugs in the upper GIT challenging, because the mobility of the macromolecules significantly increases with increasing water content, resulting in increasing drug mobility. Elevated coating levels are likely to be required. However, the permeability for larger drug molecules (e.g., proteins) can be low in polymeric networks, even at elevated water contents. In this case the mobility of the drug essentially depends on the ratio "drug molecule size: average mesh-size of macromolecular network". Advanced drug delivery systems with site specific delivery to the colon might for instance be attractive to allow for the systemic delivery of proteins after oral administration: If the proteins are effectively protected against the low pH and enzymatic degradation in the upper GIT, they might get absorbed upon release in the colon. Furthermore, the relative release rate of a poorly water-soluble drug might be very low, even if the film coating contains significant amounts of water, as long as the dosage form remains intact.

Interestingly, both, the water uptake rates and extents were higher in phosphate buffer pH 6.8 than in 0.1 M HCl, irrespective of the polymer blend ratio (FIG. 12, top row). This can be attributed to the presence of sodium dodecyl sulfate (SDS) in the aqueous ethylcellulose dispersion (acting as a stabilizer) used for film preparation. At low pH, this emulsifier is protonated and neutral, whereas at pH 6.8 it is deprotonated and negatively charged. Thus, its ability to decrease interfacial tensions is increased, facilitating water penetration into the polymeric networks.

Furthermore, the rates and extents of the dry films' mass loss significantly increased with increasing MD content (FIG. 12, bottom row). This can at least partially be explained by the leaching of this water-soluble maltodextrin into the bulk fluids. However, also the (partial) leaching of the water-soluble plasticizer TEC into the release media is responsible for this phenomenon. TEC is required for the plasticization of the ethylcellulose nanoparticles to allow for the film formation from aqueous dispersions. Even MD free films loose some dry mass, in particular at pH 6.8. The considerable water contents of the polymeric systems containing high initial MD contents can be expected to facilitate the leaching of the low molecular weight, water-soluble plasticizer TEC. Again, the observed effects were more pronounced upon exposure to phosphate buffer pH 6.8 than to 0.1 M HCl (FIG. 12), because of the presence of SDS.

When comparing MD:ethylcellulose films (FIG. 12) and BMD:ethylcellulose films (FIGS. 6 and 7) concerning their water uptake and dry mass loss its seems clear that BMD is more efficient than MD in conferring water resistance to the films.

In addition to appropriate water uptake and dry mass loss kinetics, polymeric film coatings which are intended to allow for site specific drug delivery to the colon must also provide sufficient mechanical stability in order to withstand the various mechanical stresses encountered in vivo. This concerns in particular: (i) the shear forces resulting from the motility of the upper GIT, and (ii) the hydrostatic pressure acting against the film coating from the core of the dosage form, caused by the osmotically driven water influx into the system upon contact with aqueous body fluids. In order to estimate the capacity of the investigated MD: ethylcellulose blends to withstand such external and internal stresses, the mechanical properties of thin films were measured with a texture analyzer and the puncture test. The puncture strength, % elongation at break as well as the energy required to break the films in the dry state at room temperature are shown in Table 2. Clearly, the mechanical stability of the systems increased with increasing ethylcellulose content. Thus, the latter compound is the stabilizing agent in these polymeric networks.

Figure 13:
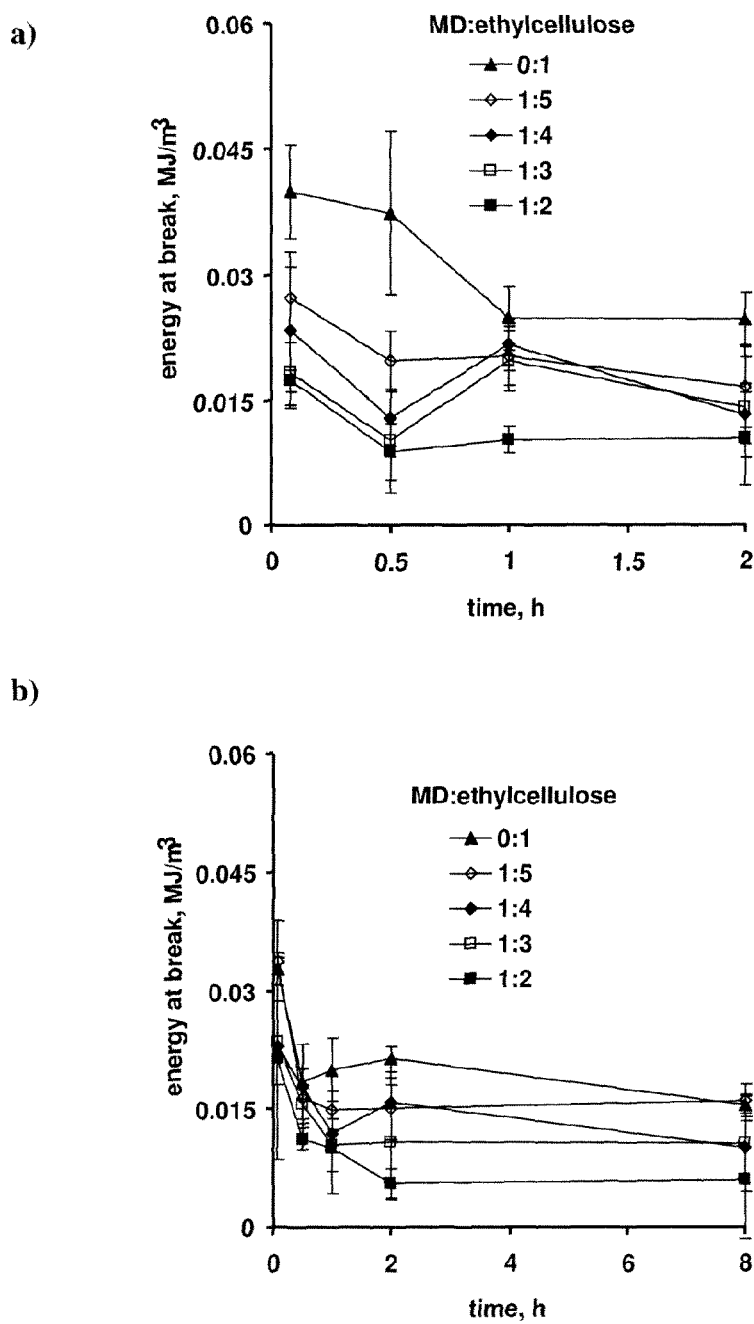
FIG. 13: Changes in the energy at break of thin maltodextrin:ethylcellulose films upon exposure to: (a) 0.1 M HCl and (b) phosphate buffer pH 6.8. The polymer blend ratio is indicated in the figures. For reasons of comparison also the results obtained with pure (plasticized) ethylcellulose films are shown.

It has to be pointed out that the mechanical properties shown in Table 2 were obtained with dry films at room temperature. It is well known that water acts as a plasticizer for many polymers and as it can be seen in FIG. 12, significant amounts of water penetrate into the films upon exposure to 0.1 M HCl and phosphate buffer pH 6.8. Furthermore, the composition of the polymeric systems significantly changes upon contact with the release media, due to (partial) MD and TEC leaching. In addition, the mechanical resistance of the polymeric films might significantly depend on the temperature. Polymers can for instance undergo glassy-to-rubbery phase transitions when increasing the temperature to 37° C. For these reasons, the mechanical properties of the investigated MD:ethylcellulose blends were also determined upon up to 2 h exposure to 0.1 M HCl and for up to 8 h exposure to phosphate buffer pH 6.8. As it can be seen in FIG. 13, the mechanical stability of the polymeric films decreased with time due to partial MD and TEC leaching, irrespective of the polymer blend ratio and type of release medium. Importantly, appropriate mechanical stabilities can effectively be adjusted by varying the polymer:polymer blend ratio (and eventually by varying the coating thickness).

Importantly, desired system stabilities can again effectively be adjusted by varying the polymer blend ratio.

The key properties of thin polymeric films consisting of polysaccharide: water insoluble polymer blends exhibiting an interesting potential to provide site specific drug delivery to the colon (and being adapted to the pathophysiology of inflammatory bowel disease patients) can effectively be adjusted by varying the polymer blend ratio and type of polysaccharides. This includes the water uptake and dry mass loss kinetics as well as the mechanical properties of the films before and upon exposure to aqueous media simulating the contents of the upper GIT. Thus, broad ranges of film coating properties can be easily be provided, being adapted to the needs of the respective drug treatment (e.g., osmotic activity of the core formulation and administered dose)

Example 3

A. Materials and Methods

A.1. Materials

Branched maltodextrin (NUTRIOSE® FB 06; Roquette Freres, Lestrem, France); aqueous ethylcellulose dispersion (Aquacoat ECD 30; FMC Biopolymer, Philadelphia, USA); triethylcitrate (TEC; Morflex, Greensboro, USA); 5-aminosalicylic acid (5-ASA; Sigma-Aldrich, Isle d'Abeau Chesnes, France); microcrystalline cellulose (Avicel PH 101; FMC Biopolymer, Brussels, Belgium); bentonite and polyvinylpyrrolidone (PVP, Povidone K 30) (Cooperation Pharmaceutique Francaise, Melun, France); pancreatin (from mammalian pancreas=mixture of amylase, protease and lipase) and pepsin (Fisher Bioblock, Illkirch, France); extracts from beef and yeast as well as tryptone (=pancreatic digest of casein) (Becton Dickinson, Sparks, USA); L-cysteine hydrochloride hydrate (Acros Organics, Geel, Belgium); cysteinated Ringer solution (Merck, Darmstadt, Germany). Pentasa®, Asacol® and Lialda are commercially available products produced by Ferring, Meduna and Shire, respectively.

A.2. Preparation of Drug-Loaded Pellet Cores

Drug-loaded pellet cores (diameter: 710-1000 μm; 60% 5-ASA, 32% microcrystalline cellulose, 4% bentonite, 4% PVP) were prepared by extrusion and spheronization. The powders were blended in a high speed granulator (Gral 10; Collette, Antwerp, Belgium) and purified water was added until a homogeneous mass was achieved. The wetted powder mixture was passed through a cylinder extruder (SK M/R; Alexanderwerk, Remscheid, Germany). The extrudates were subsequently spheronized at 520 rpm (Spheronizer Model 15; Calveva, Dorset, UK) and dried in a fluidized bed (ST 15; Aeromatic, Muttenz, Switzerland) at 40° C. for 30 min.

A.3. Preparation of Coated Pellets

BMD was dissolved in purified water (5% w/w), blended with plasticized aqueous ethylcellulose dispersion (25% TEC, overnight stirring; 15% w/w polymer content) at a ratio of 1:2, 1:3, 1:4, 1:5 (w/w) and stirred for 6 h prior to coating. The drug-loaded pellet cores were coated in a fluidized bed coater equipped with a Wurster insert (Strea 1; Aeromatic-Fielder, Bubendorf, Switzerland) until a weight gain of 5, 10, 15 and 20% (w/w) was achieved. The process parameters were as follows: inlet temperature=39±2° C., product temperature=40±2° C., spray rate=1.5-3 g/min, atomization pressure=1.2 bar, nozzle diameter=1.2 mm. After coating, the beads were further fluidized for 10 min and subsequently cured in an oven for 24 h at 60° C.

A.4. In Vitro Drug Release

Drug release from the coated pellets was measured using 3 different experimental setups, simulating the conditions in the:

(i) Upper GIT: The pellets were placed into 120 mL plastic containers, filled with 100 mL dissolution medium: 0.1 M HCl (optionally containing 0.32% pepsin) during the first 2 h, then complete medium change to phosphate buffer pH 6.8 (USP 30) (optionally containing 1% pancreatin). The flasks were agitated in a horizontal shaker (80 rpm; GFL 3033; Gesellschaft fuer Labortechnik, Burgwedel, Germany). At pre-determined time points, 3 mL samples were withdrawn and analyzed UV-spectrophotometrically ($\lambda$=302.6 nm in 0.1 M HCl; $\lambda$=330.6 nm in phosphate buffer pH 6.8) (Shimadzu UV-1650, Champs sur Marne, France). In the presence of enzymes, the samples were centrifuged for 15 min at 11,000 rpm and subsequently filtered (0.2 μm) prior to the UV measurements. Each experiment was conducted in triplicate.

(ii) Entire GIT, without feces: To simulate the gradual increase in the pH along the GIT, drug release was measured using the USP Apparatus 3 (Bio-Dis; Varian, Paris, France). Pellets were placed into 250 mL vessels filled with 200 mL 0.1 M HCl. The dipping speed was 10, or 30 dpm (as indicated). After 2 h the pellets were transferred into phosphate buffer pH 5.5 (Eur. Pharm). Table 3 indicates the subsequent changes and exposure times to the different release media. At pre-determined time points, 3 mL samples were withdrawn and analyzed UV-spectrophotometrically ($\lambda$=306.8/328.2/330.6/330.2/330.2 at pH=5.5/6.0/6.8/7.0/7.4) as described above.

(iii) Entire GIT, with feces: to simulate the transit through the upper GIT, the pellets were exposed to 0.1 M HCl for 2 h and subsequently to phosphate buffer pH 6.8 or 7.4 (USP 30) for 9 h in an USP Apparatus 3 (Bio-Dis). Afterwards, the pellets were transferred into 120 mL flasks filled with 100 mL culture medium inoculated with feces from inflammatory bowel disease patients, culture medium inoculated with a specific type of bifidobacteria, culture medium inoculated with a mixture of bifidobacteria, bacteroides and E-coli, or culture medium free of feces and bacteria for reasons of comparison. The samples were incubated at 37° C. under anaerobic conditions (5% $CO_2$, 10% $H_2$, 85% $N_2$) and gentle agitation. Culture medium was prepared by dissolving 1.5 g beef extract, 3 g yeast extract, 5 g tryptone, 2.5 g NaCl and 0.3 g L-cysteine hydrochloride hydrate in 1 L distilled water (pH 7.0±0.2) and subsequent sterilization in an autoclave. Feces of patients with Crohn's Disease or Ulcerative Colitis as well as feces of healthy subjects were diluted 1:200 with cysteinated Ringer solution; 2.5 mL of this suspension was diluted with culture medium to 100 mL. At pre-determined time points, 2 mL samples were withdrawn, centrifuged at 13,000 rpm for 5 min, filtered (0.22 μm) and analyzed for drug content using high performance liquid chromatography (HPLC; ProStar 230; Varian, Paris, France). The mobile phase consisted of 10% methanol and 90% of an aqueous acetic acid solution (1% w/v) [i]. Samples were injected into Pursuit C18 columns (150×4.6 mm; 5 μm), the flow rate was 1.5 mL/min. The drug was detected UV-spectrophotometrically at A=300 nm.3.

B Results and Discussion

B.1. Drug Release in the Upper GIT

An ideal film coating allowing for the site specific delivery of a drug to the colon should completely suppress drug release in the upper GIT. However, once the colon is reached, drug release should be time-controlled (this may include rapid and complete release). Blends of the polysaccharide BMD and ethylcellulose have been shown in preceding example as promising novel polymeric films, which show low water uptake and dry mass loss rates and extents upon exposure to release media simulating the transit though the stomach and small intestine. However, once the colon is reached, they serve as substrates for the microflora in inflammatory bowel disease patients and loose significant dry mass and take up considerable amounts of water. Yet, it was unknown whether these novel polymeric films are able to adequately control drug release from coated solid dosage forms.

Figure 14:
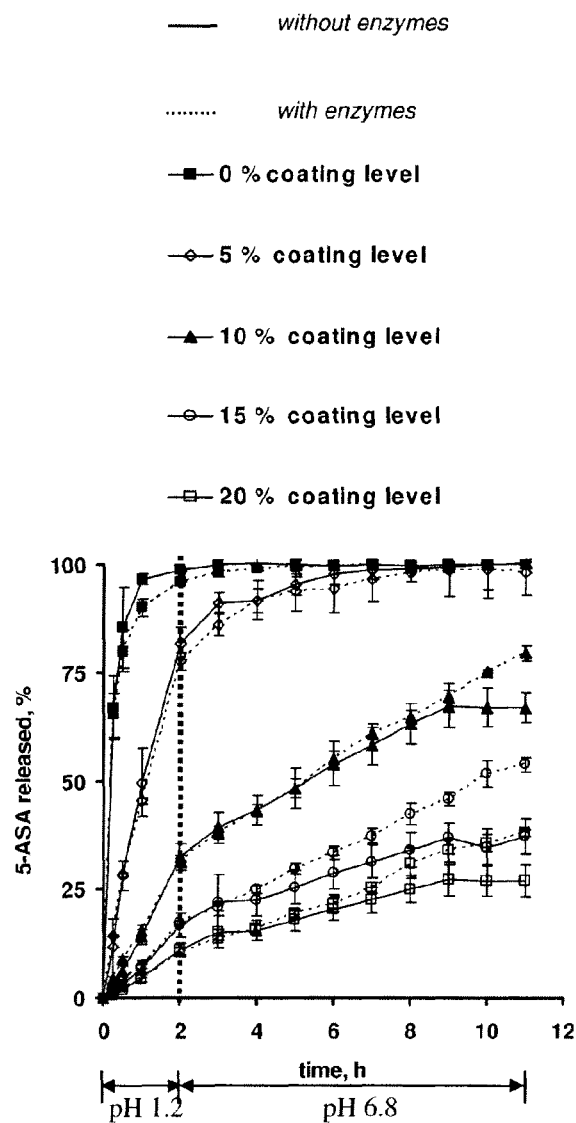
FIG. 14: In vitro release of 5-ASA from pellets coated with Branched maltodextrin:ethylcellulose blends (1:2) under conditions simulating the transit through the upper GIT. The coating level is indicated in the figure as well as the presence (dotted lines) and absence (full lines) of enzymes.

FIG. 14 shows in vitro drug release rate of 5-ASA from pellets coated with BMD:ethylcellulose 1:2 blends at different coating levels upon exposure to 0.1 M HCl for 2 h and subsequent complete medium change to phosphate buffer pH 6.8 (USP) in agitated flasks at 37° C. (solid curves). Clearly, the relative drug release rate decreased with increasing coating level, due to the increasing length of the diffusion pathways. However, even at 20% w/w coating level, drug release was still significant under these conditions, with approximately 20% of the 5-ASA being released after 11 h. It has to be pointed out that these results were obtained in release media free of enzymes. This does not appropriately reflect the conditions in vivo: The presence of digestive enzymes potentially alters the film coating properties and might result in much faster drug release. To estimate the importance of this phenomenon, 0.32% pepsin were added to the 0.1 M HCl and 1% pancreatin to the phosphate buffer pH 6.8. The dotted curves in FIG. 14 show the respective experimentally measured drug release kinetics under these conditions. Importantly, there was only a slight increase/no effect in all cases, indicating that the enzymes cannot degrade this polymeric film coating to a considerable extent under these conditions (e.g., in the presence of ethylcellulose). Nevertheless, the observed drug release rates even at higher coatings levels were too high.

Figure 15:
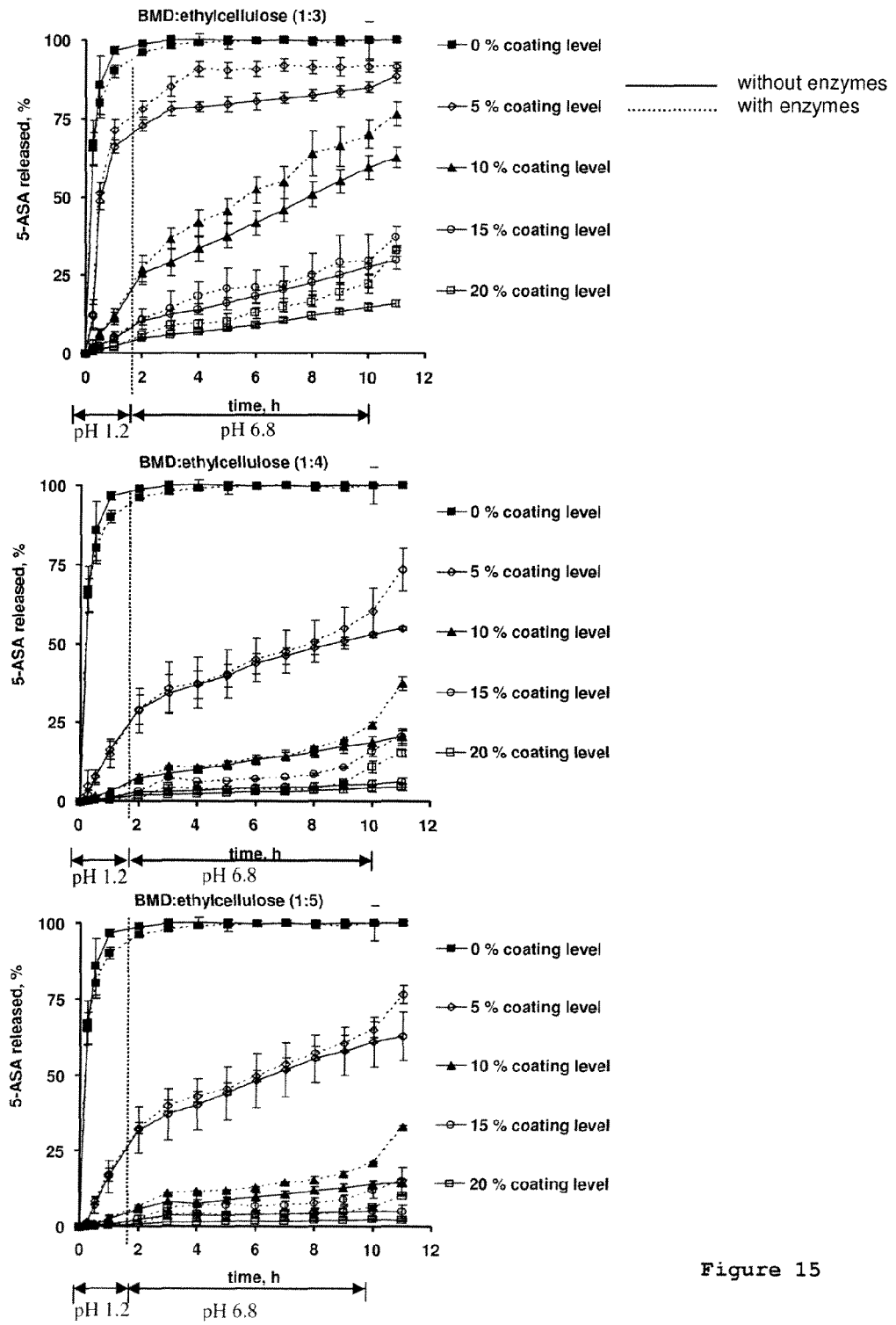
FIG. 15: Effects of the Branched maltodextrin:ethylcellulose blend ratio and coating level (indicated in the figures) on the in vitro release of 5-ASA from the investigated pellets under conditions simulating the transit through the upper GIT. Full/dotted lines indicate the absence/presence of enzymes.
Figure 16:
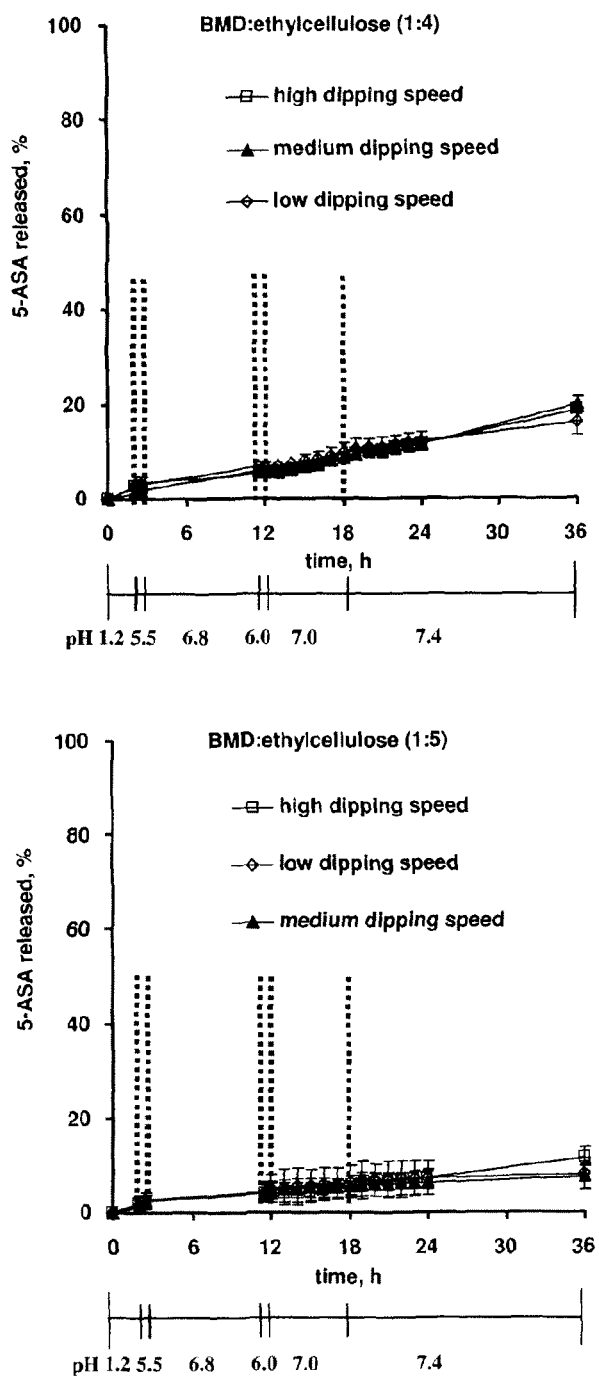
FIG. 16: Drug release from pellets coated with Branched maltodextrin:ethylcellulose blends (the ratio is indicated in the figures) at 20% coating level under conditions simulating the transit through the entire GIT (without fecal samples). High dipping speed: 30 dpm for 11.5 h, then 20 dpm. Medium dipping speed: 20 dpm for 11.5 h, then 10 dpm. Low dipping speed: 10 dpm for 11.5 h, then 5 dpm (USP Apparatus 3).

In order to decrease the release rate of 5-ASA from the investigated pellets, the initial ethylcellulose content in the film coating was increased. As previously shown, the water uptake rates and extents as well as the dry film mass loss rates and extents decreased with decreasing initial BMD contents, if free films were exposed to 0.1 N HCl and phosphate buffer pH 6.8, respectively. FIG. 15 shows the effects of the BMD:ethylcellulose blend ratio on the resulting 5-ASA release kinetics from the investigated pellets. Clearly, the relative drug release rate significantly decreased when decreasing the polymer:polymer blend ratio from 1:2 to 1:5. Furthermore, in all cases the release rate decreased with increasing coating level. As it can be seen in FIG. 15, a coating level of 15-20% at a BMD:ethylcellulose blend ratio of 1:4 or 1:5 is sufficient to almost completely suppress drug release under these conditions, simulating the transit through the upper GIT. Please note that all transit times were chosen in such a way that they can be expected to be well above the real transit time in vivo (worst case conditions) [ii,iii]. Thus, the in vivo performance of the pellets can be expected to be even better. Importantly, little to no effect was observed when adding 0.32% pepsin and 1% pancreatin to the release media, irrespective of the coating level and polymer blend ratio (dotted curves in FIG. 15). However, in these experiments the gradual increase in the pH of the release medium throughout the upper GIT was very much simplified. Furthermore, the mechanical stress the pellets were exposed to was not very important (horizontal agitation in flasks at 80 rpm). In vivo, significant mechanical shear forces (caused by the motility of the upper GIT) might induce crack formation within the polymeric film coatings, resulting in much higher drug release rates. To better simulate these two important aspects, pellets coated with 20% BMD:ethylcellulose at a blend ratio of 1:4 and 1:5 were also released in a USP apparatus 3 using the release media and transit times listed in Table 3. Three different dipping speeds were studied: (i) high: 30 dpm for 11.5 h, then 20 dpm, (ii) medium: 20 dpm for 11.5 h, then 10 dpm, and (iii) low: 10 dpm for 11.5 h, then 5 dpm. Clearly, 5-ASA release was effectively suppressed also under these more harsh conditions, in particular at the BMD:ethylcellulose blend ratio 1:5 (FIG. 16). Again, please note that the chosen release periods are non-physiological and represent extreme (worst case) conditions. The in vivo performance of these polymeric blends can be expected to be better. Thus, the mechanical stability of these film coatings is sufficient even upon exposure to considerable shear forces for prolonged periods of times.

B.2. Drug Release in the Colon

Once the colon is reached, the polymeric film coating (which effectively suppressed drug release in the upper GIT) should become permeable for the drug. FIG. 17 shows the release 5-ASA from the investigated pellets coated with 15% and 20% w/w BMD:ethylcellulose at the following three blend ratios: 1:3, 1:4, or 1:5. The release medium was 0.1 M HCl during the first 2 h, which was subsequently completely replaced by phosphate buffer pH 6.8 for 9 h. For the last 10 h the pellets were exposed to feces from inflammatory bowel disease patients and incubated under anaerobic conditions (solid curves). Clearly, 5-ASA release in the media simulating the transit through the upper GIT was effectively suppressed, whereas a significant increase in the release rate was observed once the pellets were exposed to the patients' feces. This sudden increase in the drug permeability can be attributed to the fact that BMD:ethylcellulose serve as substrates for the enzymes secreted by the microflora in patients suffering from Crohn's Disease and Ulcerative Colitis (cartoon in FIG. 17). Please note that the viability of this microflora is limited in vitro. Thus, the enzymatic activity is likely to be underestimated under the given experimental conditions. In vivo the bacteria continuously produce the respective enzymes, which are able to degrade the polysaccharide in the film coatings. Thus, the leveling of effects of drug release below 100% as observed in this study is unlikely to occur in vivo.

For reasons of comparison, 5-ASA release was also measured upon exposure to the release media simulating the conditions in the upper GIT followed by exposure to culture medium without patient's feces under anaerobic conditions (dotted curves in FIG. 17). Importantly, no sudden increase in the drug release rate was observed after 12 h. This confirms the hypothesis that the significant increase in the film coatings' permeability is caused by the (partial) enzymatic degradation of this type of polymeric systems by the enzymes present in the feces of inflammatory bowel disease patients.

Figures 18, 19:
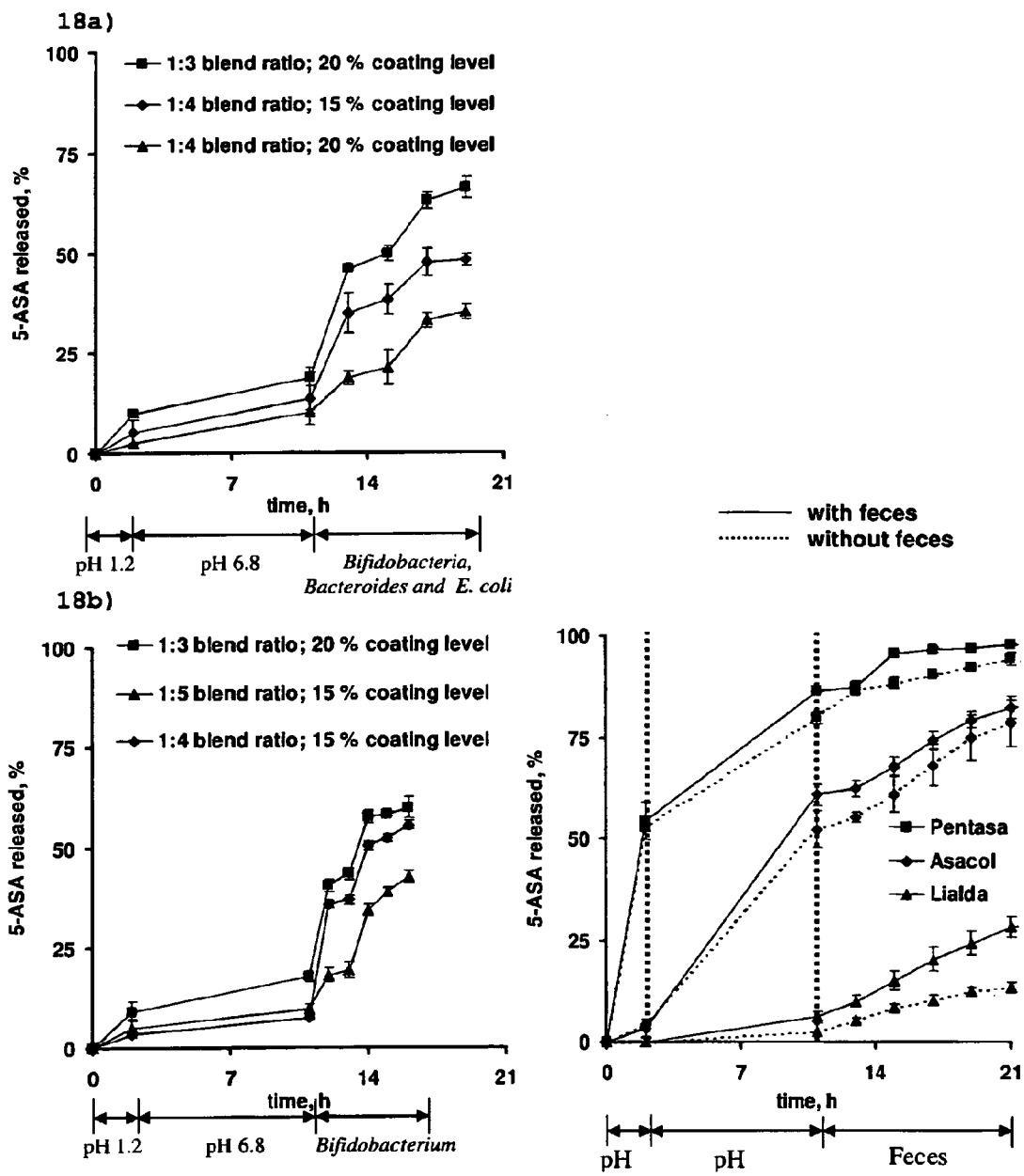
FIG. 18: 5-ASA release from pellets coated with Branched maltodextrin:ethylcellulose blends (the ratio is indicated in the figures) at 15 or 20% coating level under conditions simulating the transit through the entire GIT, with: (a) a mixture of bifidobacteria, *bacteroides* and *Escherichia coli*, or (b) *Bifidobacterium*. The dipping speed was 10 dpm.
FIG. 19: 5-ASA release from different commercially available products under conditions simulating the transit through the entire GIT, with fecal samples from inflammatory bowel disease patients. The dipping speed was 10 dpm. For reasons of comparison also drug release in culture medium without fecal samples is shown (dotted lines).

It has to be pointed out that only fresh fecal samples can be used for the in vitro drug release measurements (due to the limited viability of the complex microflora). As the availability of such samples is likely to be restricted in practice, in particular for applications in routine use, the most important bacteria in the fecal samples were to be identified and two alternative release media simulating the conditions in the colon of a subject to be developed. FIG. 18 shows the experimentally determined 5-ASA release rates from pellets coated with 15 or 20% BMD:ethylcellulose at a blend ratio of 1:3, 1:4 or 1:5, respectively. The pellets were exposed to 0.1 M HCl for the first 2 h, subsequently to phosphate buffer pH 6.8 for 9 h, and finally to either culture medium containing a mixture of bifidobacteria, *bacteroides* and *Escherichia coli* (FIG. 18a), or to culture medium containing *Bifidobacterium* (FIG. 18b). Clearly, the sudden increase in the relative release rate upon exposure to these "alternative" drug release media simulating colonic conditions was similar to the one observed in feces from inflammatory bowel disease patients (FIG. 18 versus FIG. 17). Thus, these media might be good substitutes for real fecal samples.

FIG. 19 illustrates the experimentally determined 5-ASA release kinetics from three commercially available products: Pentasa® pellets, Asacol® capsules filled with coated granules and Lialda tablets. Pentasa® pellets consist of 5-ASA loaded starter cores coated with ethylcellulose. As it can be seen, drug release already starts in the upper GIT, which is consistent with reports in the literature [iv]. Asacol® capsules are filled with 5-ASA loaded granules, which are coated with Eudragit S: a poly(acryl methacrylate), which is insoluble at low pH, but becomes soluble at pH>7. In order to be able to provide sink conditions using the Bio-Dis release apparatus and selected time schedule for media changes, hard gelatine capsules were opened and 0.05 g granules placed into each vessel. As it can be seen in FIG. 19, 5-ASA release is already significant in the upper GIT under the investigated conditions. Please note that the performance of this type of drug delivery system essentially depends on the pH of the environment the pellets are exposed to. Lialda tablets are matrices consisting of hydrophilic and lipophilic compounds [sodium-carmellose, sodium carboxymethylstarch (type A), talc, stearic acid, and carnauba wax], in which the drug is incorporated. These controlled release matrix tablets are coated with a blend of Eudragit L and Eudragit S: two poly (acryl methacrylates). As it can be seen in FIG. 19, 5-ASA release is effectively suppressed in the release media simulating the contents of the upper GIT under the investigated conditions. Once the systems are exposed to the colonic media, drug release starts. Interestingly, the presence/absence of fecal samples under these conditions did not show a very pronounced effect in any of the investigated formulations.

The newly developed BMD:ethylcellulose coated pellets provide the major advantage: (i) to be a multiple unit dosage form, allowing for less variability in the gastric transit times, a more homogeneous distribution throughout the contents of the GIT and the avoidance of the "all-or-nothing" effect of single unit dosage forms, (ii) to effectively suppress drug release in the upper GIT, (iii) to provide time-controlled drug release in the colon, the onset of which is induced by enzymes that are present in the colon of inflammatory bowel diseases, (iv) to contain the polysaccharide BMD, which pre-biotic activity is surprisingly not inhibited when mixed with the ethylcellulose, normalizing the microflora in the patients' colon.

The novel polymeric films coatings BMD: ethylcellulose blends allows according to the invention, the site specific delivery of drugs (e.g., 5-ASA) to the colon. Importantly, these new polymeric barriers are adapted to the conditions at the target site, especially with respect to the microflora in the disease state and pH of the environment. Furthermore, the second effect of this novel polymeric films coating is the significant pre-biotic effects of the BMD, normalizing the microflora in the colon, which is particularly beneficial for patients suffering from inflammatory bowel diseases.

Example 4

Figure 20:
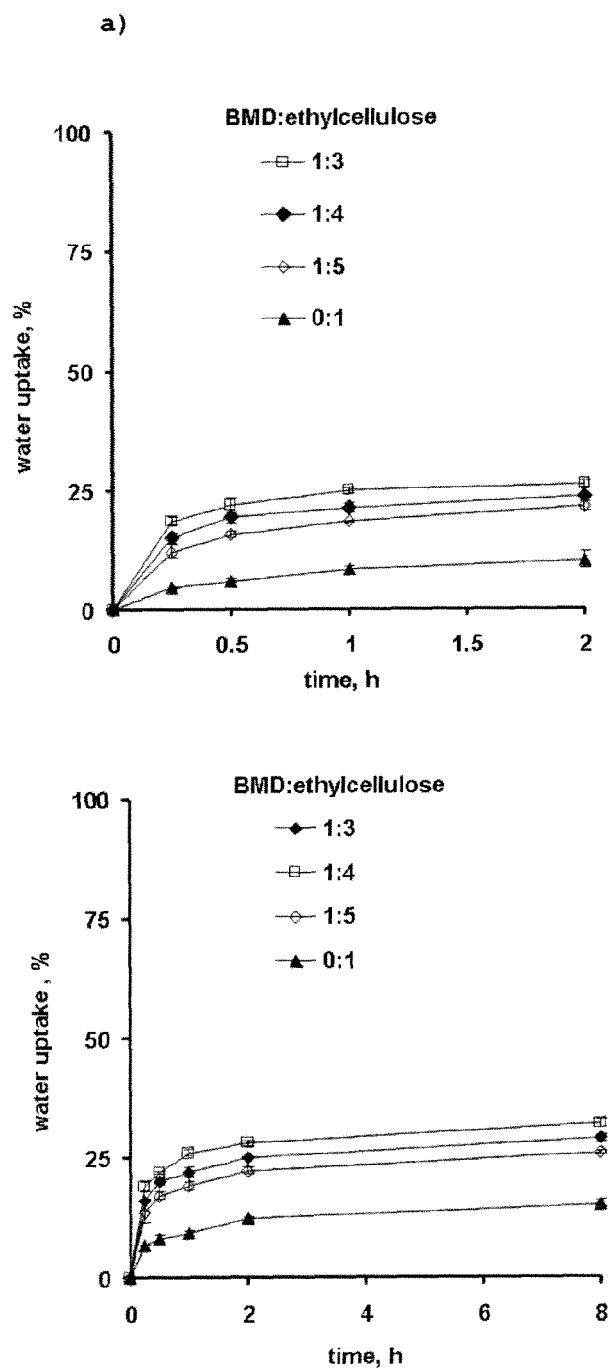
FIG. 20: Water uptake kinetics of thin NUTRIOSE:ethylcellulose films upon exposure to: (a) 0.1 M HCl, and (b) phosphate buffer pH 6.8. The polymer:polymer blend ratio (w:w) is indicated in the diagrams. Ethylcellulose was plasticized with 25% dibutyl sebacate.
Figure 25:
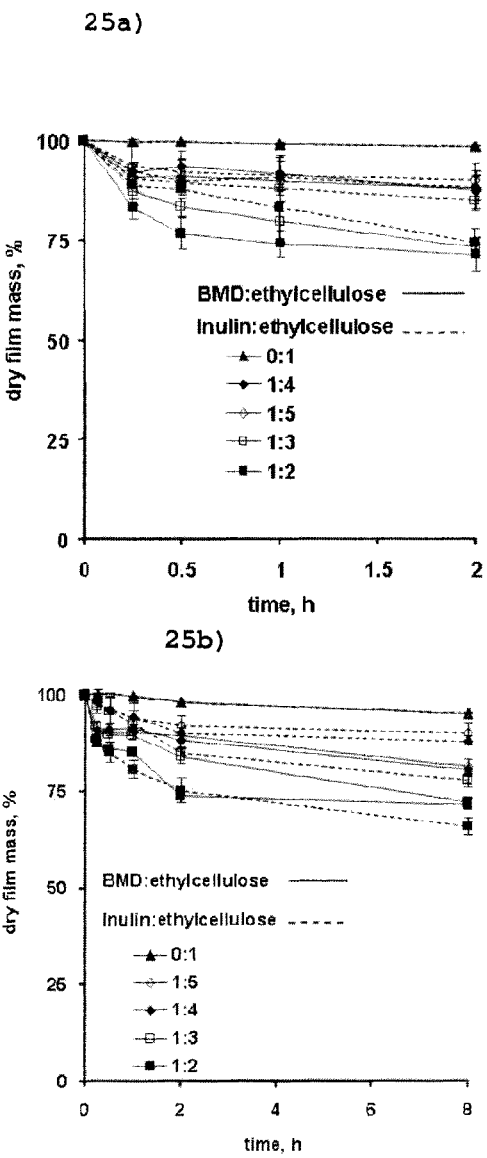
FIG. 25: Dry mass loss of thin films consisting of Branched maltodextrin:ethylcellulose (full lines) and Inulin:ethylcellulose at the following ratios 0:1; 1:2; 1:3; 1/4 and 1:5 upon exposure to: (a) 0.1 M HCl and (b) phosphate buffer pH 6.8 (TEC content, referred to the ethylcellulose mass: 25% w/w).
Figure 26:
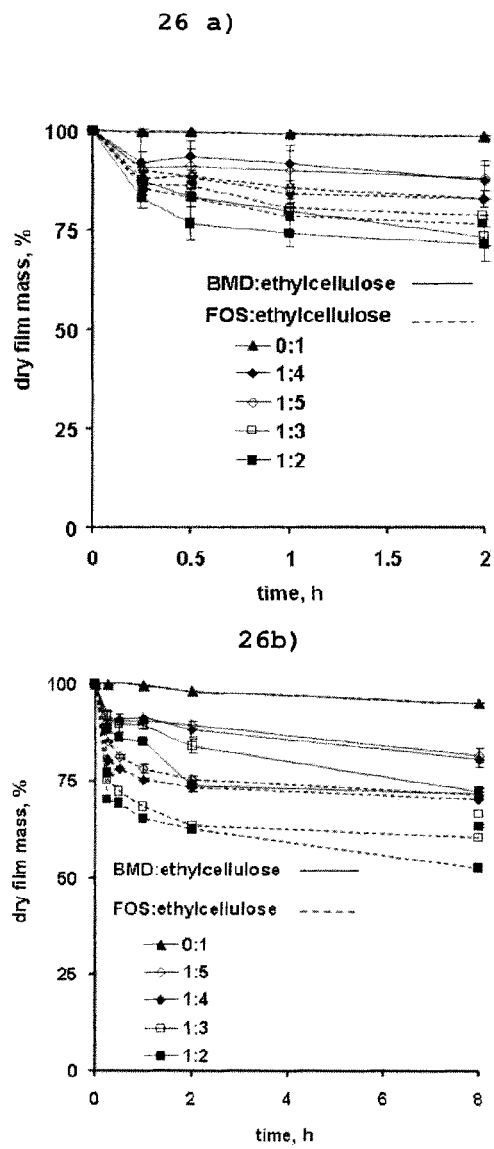
FIG. 26: Dry mass loss of thin films consisting of Branched maltodextrin:ethylcellulose (full lines) and FOS:ethylcellulose at the following ratios 0:1; 1:2; 1:3; 1/4 and 1:5 upon exposure to: (a) 0.1 M HCl and (b) phosphate buffer pH 6.8 (TEC content, referred to the ethylcellulose mass: 25% w/w).

BMD:ethylcellulose coated pellets are obtained, using the same protocol than example 2 and 3 with 25% dibutyl sebacate as plasticizer. Water uptake kinetics (FIG. 20) and Dry mass loss kinetics are studied (FIG. 21) showing same results than BMD: ethylcellulose coated pellets using TEC as plasticizer. Indeed, the coated pellets characteristics are not plasticizer dependent. 5-ASA release is studied using the pellets coated with BMD:ethylcellulose 1:4 (ethylcellulose being plasticized with 25% dibutyl sebacate) under conditions simulating the transit through the entire GIT, in the presence and absence of feces from inflammatory bowel disease patients according to the same protocol than example 3. The coating level was 15% (FIG. 22). Similarly to preceding example 3, 5-ASA release is not observed in the release media simulating the contents of the upper GIT under the investigated conditions. Once the systems are exposed to the colonic media, drug release starts.

Example 5

A. Materials and Methods

A.1. Materials

Branched maltodextrin (BMD) (a water-soluble, branched maltodextrin with high fiber contents obtained from wheat starch; NUTRIOSE® FB 06, Roquette Freres, Lestrem, France); Inulin, FOS; aqueous ethylcellulose dispersion (Aquacoat ECD 30; FMC Biopolymer, Philadelphia, USA); triethylcitrate (TEC; Morflex, Greensboro, USA).

A.2. Preparation of Thin, Polymeric Films

Thin polymeric films were prepared as seen in example 2.

A.3. Film Characterization

The thickness, water uptake and dry mass loss kinetics of the films were measured as seen in example 2

B Results and Discussion

Water Uptake and Dry Mass Loss of Thin Films

Inulin and FOS water uptake and dry mass loss kinetics were compared to BMD upon exposure to 0.1 M HCl and phosphate buffer pH 6.8 at 37° C. Clearly, the polymer blend ratio significantly affected the resulting water penetration rates and extents for the FOS and Inulin as observed for BMD. As previously seen, this phenomenon can be attributed to the more hydrophobic nature of ethylcellulose compared to the water-soluble indigestible polysaccharides Inulin, FOS and BMD. Interestingly, the water uptake rates and extents of the investigated films were higher in phosphate buffer pH 6.8 than in 0.1 N HCl (FIG. 23b versus FIG. 23a and FIG. 24b versus FIG. 24a) previously attributed to the presence of the emulsifier sodium dodecyl sulfate (SDS) in the aqueous ethylcellulose dispersion Aquacoat ECD.

Comparing the water uptake rates and extents of the films upon exposure to 0.1 M HCl and phosphate buffer pH 6.8 in FIGS. 23 to 26, it can be seen that the type of second polysaccharide has a significant impact. For instance, BMD:ethylcellulose blends (full lines) show the lowest water uptake rates and dry mass loss, irrespective of the type of release medium. Even if Inulin and FOS are less efficient than BMD in conferring to the films a water resistance behavior, premature drug release within the upper GIT can be expected to be limited with Inulin and FOS containing polymeric films, irrespective of the polymer:polymer blend ratio in the investigated range.

Example 6

A. Materials and Methods

A.1 Materials 2,4,6-Trinitrobenzene sulfonic acid (TNBS) (Sigma-Aldrich, Isle d'Abeau Chesnes, France); cysteinated Ringer solution (Merck, Darmstadt, Germany); BMD (NUTRIOSE® FB 06; Roquette Freres, Lestrem, France); Peas starch N-735 (peas starch; Roquette Freres, Lestrem, France); aqueous ethylcellulose dispersion (Aquacoat ECD 30; FMC Biopolymer, Philadelphia, USA); triethylcitrate (TEC; Morflex, Greensboro, USA); 5-aminosalicylic acid (5-ASA; Sigma-Aldrich, Isle d'Abeau Chesnes, France); microcrystalline cellulose (Avicel PH 101; FMC Biopolymer, Brussels, Belgium); polyvinylpyrrolidone (PVP, Povidone K 30) (Cooperation Pharmaceutique Francaise, Melun, France); Pentasa® (coated pellets, Ferring, batch number: JX 155), Asacol® (coated granules, Meduna, batch number: TX 143).

A.2 Preparation of BMD: Ethylcellulose and Peas Starch: Ethylcellulose Coated Pellets 5-Amino salicylic acid (5-ASA) loaded pellet starter cores (diameter: 0.7-1.0 mm; 60% 5-ASA, 32% microcrystalline cellulose, 4% bentonite, 4% PVP) were prepared by extrusion and subsequent spheronisation as follows: The respective powders were blended in a high speed granulator (Gral 10; Collette, Antwerp, Belgium) and purified water was added until a homogeneous mass was obtained (41 g of water for 100 g of powder blend). The wetted mixture was passed through a cylinder extruder (SK M/R, holes: 1 mm diameter, 3 mm thickness, rotation speed: 96 rpm; Alexanderwerk, Remscheid, Germany). The extrudates were subsequently spheronised at 520 rpm for 2 min (Spheroniser Model 15; Calveva, Dorset, UK) and dried in a fluidized bed (ST 15; Aeromatic, Muttenz, Switzerland) at 40° C. for 30 min. The size fraction 0.7-1.0 mm was obtained by sieving.

The obtained drug loaded starter cores were subsequently coated in a fluidized bed coater, equipped with a Wurster insert (Strea 1; Aeromatic-Fielder, Bubendorf, Switzerland) with BMD:ethylcellulose 1:4 blends (BMD:EC coated pellets) or with peas starch: ethylcellulose 1:2 blends (peas starch: EC coated pellets) until a weight gain of 15% (w/w) (BMD:EC coated pellets) or 20% (w/w) (peas starch: EC coated pellets) was achieved.

BMD was dissolved in purified water (5% w/w), blended with plasticized aqueous ethylcellulose dispersion (25% TEC, overnight stirring; 15% w/w polymer content) at a ratio of 1:4 (w/w, based on the non-plasticized polymer dry mass) and stirred for 6 h prior to coating. The drug-loaded pellet cores were coated in a fluidized bed coater equipped with a Wurster insert (Strea 1; Aeromatic-Fielder, Bubendorf, Switzerland) until a weight gain of 15% (w/w) was achieved. The process parameters were as follows: inlet temperature=39±2° C., product temperature=40±2° C., spray rate=1.5-3 g/min, atomization pressure=1.2 bar, nozzle diameter=1.2 mm. After coating, the beads were further fluidized for 10 min and subsequently cured in an oven for 24 h at 60° C.

Peas starch was dispersed in purified water at 65-75° C. (5% w/w). Aqueous ethylcellulose dispersion (15% w/w solids content) was plasticized for 24 h with 25% TEC (w/w, referred to the solids content of the dispersion). The peas starch and ethylcellulose dispersions were blended at room temperature at the following ratio: 1:2 (polymer:polymer, w:w). The mixture was stirred for 6 h prior to coating. The drug-loaded pellet cores were coated in a fluidized bed coater equipped with a Wurster insert (Strea 1; Aeromatic-Fielder, Bubendorf, Switzerland) until a weight gain of 20% (w/w) was achieved. The process parameters were as follows: inlet temperature=39±2° C., product temperature=40±2° C., spray rat=1.5-3 g/min, atomization pressure=1.2 bar, nozzle diameter=1.2 mm. Afterwards, the pellets were further fluidized for 10 min and subsequently cured in an oven for 24 h at 60° C.

A.3 Induction of Colitis and Study Design

Male Wistar rats (250 g) were used for the in vivo study, which was conducted in accredited establishment at the Institut Pasteur de Lille (A 35009), according to governmental guidelines (86/609/CEE). Four animals were housed per cage, all rats had free access to tap water.

At the beginning of the experiment (day 0), the rats were divided in six groups (5-8 animals/group). Two groups received standard chow (negative and positive control groups). The other groups received food with either Pentasa® pellets (n=8), Asacol® pellets (n=8), BMD:ethylcellulose coated pellets (n=8) or peas starch: ethylcellulose coated pellets (n=8). These four different chows were prepared using the "food admix" technique. All systems were added to obtain a dose of 5-ASA of 150 mg/kg/day.

At day 3, colitis was induced as follows: The rats were anesthetized for 90-120 min using pentobarbital (40 mg/kg) and received an intrarectal administration of TNBS (250 μl, 20 mg/rat) dissolved in a 1:1 mixture of an aqueous 0.9% NaCl solution with 100% ethanol. Control rats (negative control) received an intrarectal administration of the vehicle only (1:1 mixture of an aqueous 0.9% NaCl solution with 100% ethanol). Animals were sacrificed 3 days after intrarectal TNBS or vehicle administration (day 6).

A.4 Macroscopic and Histological Assessment of Colitis

Macroscopic and histological indications of colitis were evaluated blindly by two investigators. A colon specimen located precisely 4 cm above the anal canal was used for histological evaluation according to the Ameho criteria. This grading on a scale from 0 to 6 takes into account the degree of inflammation infiltrate, the presence of erosion, ulceration, or necrosis, and the depth and surface extension of lesions.

A.5 Statistics

All comparisons were analyzed using the nonparametric test (Mann-Whitney) test. Differences were judged statistically significant if the P value was <0.05.

B Results and Discussion

TNBS-induced colitis is improved by the treatment with BMD:ethylcellulose coated pellets and peas starch:ethylcellulose coated pellets.

Figure 27:
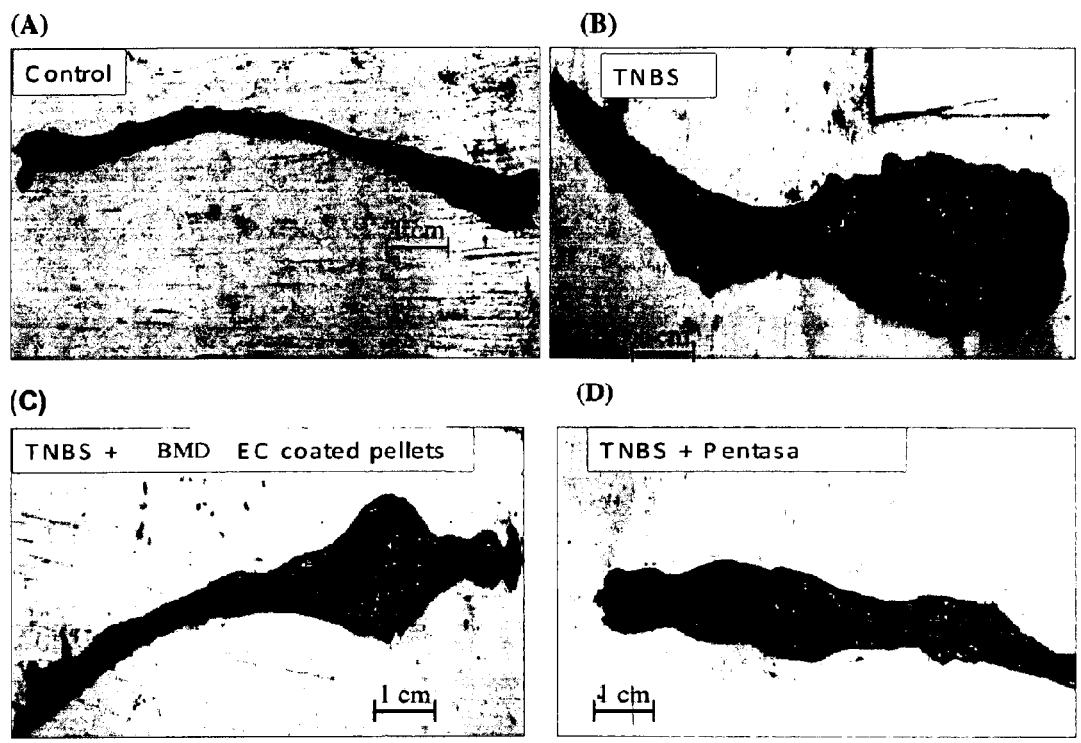
FIG. 27: Macroscopic appearance of the colon of rats, receiving: (A) vehicle only intrarectally (negative control group), (B) TNBS intrarectally (positive control group), (C) TNBS intrarectally and BMD: EC coated pellets orally, or (D) TNBS intrarectally and Pentasa® pellets orally. TNBS/the vehicle only was administered intrarectally on day 3. The orally administered dose of 5-ASA was 150 mg/kg/day.

The development of colitis in animals subjected to intrarectal TNBS administration was characterized. Control rats (negative control group), sacrificed 3 days after intrarectal administration of the vehicle only (a 1:1 mixture of an aqueous 0.9% NaCl solution with 100% ethanol), had no macroscopic lesions in the colon (FIG. 27A). In contrast, a severe colitis was induced as early as 3 d after administration of TNBS (FIG. 27B). On the histological level, no abnormalities were detected in control rats (FIG. 29: control=negative control group). In contrast, 3 days after the administrations of TNBS, colon histology was characterized by large areas of ulceration with a neutrophilic infiltrate, necrosis extending deeply into the muscular layer (FIG. 29: TNBS). The colon of animals treated with BMD:ethylcellulose coated pellets showed a significant reduction of the lesion (FIG. 27). The results were similar for rats treated with peas starch:ethylcellulose coated pellets (data not shown). Furthermore, the effects of treatments with Pentasa® pellets, Asacol® pellets, BMD:ethylcellulose coated pellets and peas starch:ethylcellulose coated pellets on TNBS-induced colon lesions were studied using the Ameho score (FIG. 28). Untreated rats with colitis were investigated for reasons of comparison. Optimal effects were obtained with BMD:ethylcellulose coated pellets and with peas starch:ethylcellulose coated pellets. Three days after induction of colitis, a significant decrease in the macroscopic lesion score was observed in rats that had received BMD:ethylcellulose coated pellets and peas starch:ethylcellulose coated pellets preventively compared with untreated rats with colitis. Parallel to the macroscopic inflammation, histological analysis also confirmed major differences between animals treated with: (i) TNBS intrarectally, (ii) TNBS intrarectally and Pentasa® pellets orally, (iii) TNBS intrarectally and Asacol® pellets orally, (v) TNBS intrarectally and BMD:ethylcellulose coated pellets orally, and (v) TNBS intrarectally and peas starch:ethylcellulose coated pellets orally (FIG. 30). This was reflected by a significant decrease of the Ameho inflammation score at 3 d after TNBS administration (FIG. 28). Clearly, the administration of BMD:ethylcellulose coated pellets and of peas starch: ethylcellulose coated pellets reduced the inflammatory lesions which consisted of smaller polymorphic inflammatory infiltrates, limited edema and small focal necrosis lesions (FIG. 29). Thickening of the colon wall, with a predominant inflammatory infiltrate in the lamina propria, and necrosis extending deeply into the muscular and serosal layer are evident in the case of treatment with TNBS, TNBS and Pentasa® pellets and TNBS and Asacol® pellets.

These results clearly proof the efficacy of the proposed novel film coatings for colon targeting in vivo.

TABLE 1

|  | Healthy subjects | Crohn's Disease | Ulcerative Colitis |
|---|---|---|---|
| Number | 10 | 11 | 5 |
| Mean age | 40 +/− 15 | 32 +/− 12 | 36 +/− 20 |
| Mean total counts [log UFC/g] | 9.88 +/− 0.48 | 9.15 +/− 1.30 | 9.88 +/− 0.57 |
| Number of strains | 28 | 34 | 14 |
| Mean | 2.8 | 3.1 | 2.8 |
| Anaerobes | | | |
| *Bacteroides* | 9 | 10 | 3 |
| *Prevotella* | 2 | 2 | 2 |
| *Fusobacterium* | 3 | 3 | 2 |
| *Veillonella* | 0 | 0 | 1 |
| *Clostridium* | 0 | 5 | 1 |
| *Bifidobacterium* | 9 | 3 | 1 |
| Other Gram + rods | 3 | 2 | 2 |
| Gram + cocci | 1 | 2 | 0 |
| Aerobes | | | |
| Enterobacteria | 1 | 3 | 2 |
| *Escherichia coli* | 1 | 2 | 1 |
| *Citrobacter freundii* | 0 | 2 | 1 |
| *Lactobacillus* | 0 | 2 | 0 |
| *Streptococcus* | 0 | 2 | 0 |
| Mean counts McConkey agar | 6.30 +/− 1.19 | 7.16 +/− 1.48 | 8.01 +/− 1.06 |
| Number of strains | 10 | 14 | 8 |
| *Escherichia coli* | 10 | 6 | 4 |
| *E. coli* lac- | 0 | 1 | 0 |
| *Citrobacter freundii* | 0 | 3 | 1 |
| *Klebsiella pneumoniae* | 0 | 1 | 1 |
| *Klebsiella oxytoca* | 0 | 2 | 0 |
| *Enterobacter cloacae* | 0 | 1 | 0 |
| Other Gram-rods | 0 | 0 | 1 |

TABLE 2

| | Blend ratio | Puncture strength ± (s), MPa | Elongation at break ± (s), % | Energy at break ± (s), MJ/m³ |
|---|---|---|---|---|
| MD | 1:2 | 0.34 ± (0.05) | 0.43 ± (0.08) | 0.012 ± (0.005) |
| | 1:3 | 0.36 ± (0.09) | 0.57 ± (0.05) | 0.014 ± (0.006) |
| | 1:4 | 0.43 ± (0.07) | 0.53 ± (0.04) | 0.011 ± (0.003) |
| | 1:5 | 0.42 ± (0.11) | 0.58 ± (0.07) | 0.015 ± (0.009) |
| PS HP-PG | 1:2 | 0.45 ± (0.04) | 0.55 ± (0.09) | 0.016 ± (0.008) |
| | 1:3 | 0.40 ± (0.03) | 0.53 ± (0.07) | 0.012 ± (0.007) |
| | 1:4 | 0.42 ± (0.09) | 0.60 ± (0.09) | 0.016 ± (0.008) |
| | 1:5 | 0.50 ± (0.08) | 0.60 ± (0.05) | 0.020 ± (0.004) |
| MS7 A-PG | 1:2 | 0.78 ± (0.09) | 0.63 ± (0.02) | 0.061 ± (0.005) |
| | 1:3 | 0.84 ± (0.05) | 0.67 ± (0.08) | 0.065 ± (0.009) |
| | 1:4 | 0.85 ± (0.04) | 0.66 ± (0.07) | 0.070 ± (0.011) |
| | 1:5 | 0.87 ± (0.05) | 0.75 ± (0.02) | 0.073 ± (0.006) |
| MS6 A-PG | 1:2 | 0.60 ± (0.01) | 0.50 ± (0.07) | 0.052 ± (0.002) |
| | 1:3 | 0.52 ± (0.05) | 0.75 ± (0.10) | 0.068 ± (0.008) |
| | 1:4 | 0.76 ± (0.02) | 0.82 ± (0.04) | 0.077 ± (0.006) |
| | 1:5 | 0.77 ± (0.03) | 0.81 ± (0.06) | 0.075 ± (0.010) |
| MS6 HP-PG | 1:2 | 0.53 ± (0.07) | 0.72 ± (0.05) | 0.053 ± (0.010) |
| | 1:3 | 0.64 ± (0.03) | 0.81 ± (0.07) | 0.066 ± (0.009) |
| | 1:4 | 0.63 ± (0.02) | 0.82 ± (0.07) | 0.062 ± (0.009) |
| | 1:5 | 0.87 ± (0.03) | 0.77 ± (0.05) | 0.070 ± (0.010) |

TABLE 3

| Simulated GI segment | Exposure time | Release medium | pH |
|---|---|---|---|
| Stomach | 2 h | 0.1 M HCl | 1.2 |
| Duodenum | 0.5 h | Phosphate buffer (Eur. Pharm. 5) | 5.5 |
| Jejunum-Ileum | 9 h | Phosphate buffer (USP 30) | 6.8 |
| Caecum | 0.5 h | Phosphate buffer (USP 30) | 6.0 |
| Proximal Colon | 6 h | Phosphate buffer (USP 30) | 7.0 |
| Distal Colon | 18 h | Phosphate buffer (USP 30) | 7.4 |

The invention claimed is:

1. A controlled release delivery dosage form for controlled release of an active ingredient in the colon of patients, comprising an active ingredient coated by a polymeric mixture of:
   (i) ethyl cellulose, and
   (ii) at least an indigestible maltodextrin or at least an indigestible dextrin having between 15 and 35% of 1→6 glucoside linkages, a reducing sugar content of less than 20%, a polymolecularity index of less than 5 and a number-average molecular mass Mn at most equal to 4500 g/mol,
said controlled release delivery dosage form comprising a core, the active ingredient being dispersed or dissolved in said core,
wherein the indigestible maltodextrin or indigestible dextrin: ethyl cellulose ratio is between 1:2 and 1:8.

2. The controlled release delivery dosage form according to claim 1, wherein the indigestible maltodextrin or indigestible dextrin:ethyl cellulose ratio is between 1:3 and 1:6.

3. The controlled release delivery dosage form according to claim 1, wherein the core has a coating level of 5% to 30%.

4. The controlled release delivery dosage form according to claim 3, wherein the core has a coating level of 10% to 20%.

5. The controlled release delivery dosage form according to claim 1, wherein the polymeric mixture comprises a plasticizer.

6. The controlled release delivery dosage form according to claim 1, further comprising a water insoluble polymer selected from the group consisting of acrylic and/or methacrylic ester polymers, polymers or copolymers of acrylate or methacrylate, polyvinyl esters, polyvinyl acetates, polyacrylic acid esters, and butadiene styrene copolymers, methacrylate ester copolymers, cellulose acetate phtalate, polyvinyl acetate phtalate, shellac, methacrylic acid copolymers, cellulose acetate trimellitate, hydroxypropyl methylcellulose phtalate, zein, starch acetate.

7. The controlled release delivery dosage form according to claim 5, wherein the plasticizer is a water soluble plasticizer.

8. The controlled release delivery dosage form according to claim 1, wherein said controlled release pharmaceutical composition is a multiparticulate dosage form.

9. A method for preparing a controlled release delivery dosage form for controlled release of an active ingredient in the colon of patients having a colonic microflora imbalance or in the colon of healthy subjects, said method comprising:
   (a) forming a polymeric mixture of:
      (i) ethyl cellulose, and
      (ii) at least an indigestible maltodextrin or at least an indigestible dextrin having between 15 and 35% of 1→6 glucoside linkages, a reducing sugar content of less than 20%, a polymolecularity index of less than 5 and a number-average molecular mass Mn at most equal to 4500 g/mol,
   (b) coating said active ingredient by the polymeric mixture.

10. A method of stimulating the growth and/or activity of bacteria in the digestive system, comprising:

administering to a patient in need thereof an effective amount of a controlled release dosage form for controlled release of an active ingredient in the colon of patients, said controlled release dosage form comprising an active ingredient coated by a polymeric mixture of:

(i) ethyl cellulose, and (ii) at least an indigestible maltodextrin or at least an indigestible dextrin having between 15 and 35% of 1→6 glucoside linkages, a reducing sugar content of less than 20%, a polymolecularity index of less than 5 and a number-average molecular mass Mn at most equal to 4500 g/mol, and said controlled release delivery dosage form comprising a core, the active ingredient being dispersed or dissolved in said core, wherein the indigestible maltodextrin or indigestible dextrin: ethyl cellulose ratio is between 1:2 and 1:8.

11. The controlled release delivery dosage form according to claim 6, wherein the polymeric mixture comprises a water soluble plasticizer, the plasticizer being selected from the group consisting of polyols, organic esters, oils or glycerides, soya lecithin, and mixtures thereof.

12. The controlled release delivery dosage form according to claim 5, wherein the polymeric mixture comprises a plasticizer in a content between 25% to 30% w/w referred to the water insoluble polymer content.

13. The controlled release delivery dosage form according to claim 7, wherein the plasticizer is selected from the group consisting of polyols, organic esters, oils or glycerides, soya lecithin, and mixtures thereof.

14. The method according to claim 9, wherein the indigestible maltodextrin: ethyl cellulose ratio is between 1:2 and 1:8.

* * * * *